(12) United States Patent
Ballinger et al.

(10) Patent No.: US 6,548,634 B1
(45) Date of Patent: Apr. 15, 2003

(54) SYNTHETIC PEPTIDES HAVING FGF RECEPTOR AFFINITY

(75) Inventors: Marcus Ballinger, Burlingame, CA (US); Michael Kavanaugh, Danville, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/407,687

(22) Filed: Sep. 28, 1999

Related U.S. Application Data

(60) Provisional application No. 60/102,667, filed on Sep. 30, 1998, and provisional application No. 60/134,120, filed on May 14, 1999.

(51) Int. Cl.[7] .......................... C07K 7/00; A61K 38/04; G01N 33/53; C12N 5/00
(52) U.S. Cl. ...................... 530/326; 530/327; 435/7.2; 435/325
(58) Field of Search ................. 435/7.2, 325; 530/326, 530/327

(56) References Cited

U.S. PATENT DOCUMENTS 5,670,153 A * 9/1997 Weiner et al. ............ 424/189.1
5,684,129 A * 11/1997 Fish ............................. 530/326

FOREIGN PATENT DOCUMENTS

| EP | 0 246 753 A2 | | 11/1987 |
| WO | 92/13958 | | 8/1992 |
| WO | 98/21237 | | 5/1998 |
| WO | WO 98/21237 | * | 5/1998 |
| WO | 00/03245 | | 1/2000 |

OTHER PUBLICATIONS

Yayon, A. et al. Isolation of peptides that inhibit binding of basic fibroblast growth factor to its receptor from a random phage–epitope library. Proc. Natl. Acad. Sci. USA 1993 90;10643–10647.*

Mikayama T. Molecular cloning and functional expression of a cDNA encoding glycosylation–inhibiting factor. Proc. Natl. Acad. Sci. USA vol. 90, pp. 10056–10060, 1993.*

Voet et al. Biochemistry. 1990. John Wiley & Sons, Inc.. pp. 126–128 and 228–234.*

Schettler, et al. Release of proteinases from stimulated polymorphonuclear leukocytes. Evidence for subclasses of the main granule types and their association with cytoskeletal components. Eur J Biochem. Apr. 10, 1991; 197(1):197–202.*

Ballinger, Marcus D., et al., "Semirational Design of a Potent, Artificial Agonist of Fibroblast Growth Factor Receptors," *Nature Biotechnology* (Dec. 1999) vol. 17:1199–1204.

Yayon, Avner, et al., "Isolation of Peptides That Inhibit Binding of Basic Fibroblast Growth Factor to Its Receptor from a Random Phage–Epitope Library," *Proc. Natl. Acad. Sci. USA* (Nov. 1993) vol. 90:10643–10647.

* cited by examiner

*Primary Examiner*—David S. Romeo
*Assistant Examiner*—Joseph F. Murphy
(74) *Attorney, Agent, or Firm*—Robert P. Blackburn; Lisa E. Alexander; Paula A. Borden

(57) ABSTRACT

Peptidic compositions having FGF receptor affinity, as well as fusion proteins and oligomers of the same, are provided. The subject peptidic compounds are characterized by having little or no homology to naturally occurring bFGF. The subject fusion proteins include the peptidic composition linked to an oligomerization domain, either directly or through a linking group and optionally further include a heparin binding domain. The subject peptidic compositions, fusion proteins and oligomers thereof find use in a variety of applications, including both research and therapeutic applications, in which FGF receptor ligands are employed.

12 Claims, 7 Drawing Sheets

[a]Containing the fixed AE sequence at the front but not the PPPPPP C-terminal linker.

Jun dimer

IgG fusion dimer

[a]Containing the fixed AE sequence at the front but not the PPPPPP C-terminal linker.

```
          10                  20                  30                  40                  50                  60
GCT GAA TCG GGC GAT GAC TAT TGC GTT TTC CTC GTT TTC ACC GAC TCT GCG TGG ACA AGG ATC
CGA CTT AGC CCG CTA CTG ATA ACG CAA GAG CAA AAG TGG CTG AGA CGC ACC TGT TTC TAG
Ala Glu Ser Gly Asp Asp Tyr Cys Val Leu Val Phe Thr Asp Ser Ala Trp Thr Lys Ile ^  ^
 a    a    a    a    a    TRANSLATION OF UNTITLED1 [A]  a    a    a    a    a 70                  80                  90                  100                 110                 120
TGT GAT TGG AGC CAT TTT CGG AAT GGG CCC GGA GGA TCA GGT GGA GGA AGC GGA GGT
ACA CTA ACC TCG GTA AAA GCC TTA CCC GGG CCT CCT AGT CCA CCT CCT TCG CCT CCA
Cys Asp Trp Ser His Phe Arg Asn Gly Pro Gly Gly Ser Gly Gly Gly Ser Gly Gly ^  ^
 a    a    a    a    a    TRANSLATION OF UNTITLED1 [A]  a    a    a    a    a 130                 140                 150                 160                 170                 180
GGT TCG GGA GGT GGA AGC GGA GGT GGT TCT AGA TGC GGT GGT CGT ATC GCC CGG CTG GAA
CCA AGC CCT CCA CCT TCG CCT CCA CCA AGA TCT ACG CCA CCA GCA TAG CGG GCC GAC CTT
Gly Ser Gly Gly Gly Ser Gly Gly Gly Ser Arg Cys Gly Gly Arg Ile Ala Arg Leu Glu ^  ^
 a    a    a    a    a    TRANSLATION OF UNTITLED1 [A]  a    a    a    a    a 190                 200                 210                 220                 230                 240
GAA AAA GTT AAG ACT CTG AAA GCG CAA AAC TCT GAA CTG GCT TCC ACC GCA AAC ATG CTC
CTT TTT CAA TTC TGA GAC TTT CGC GTT TTG ACT TTG AGA CTT GAC CGA AGG TGG CGT TTG TAC GAG
Glu Lys Val Lys Thr Leu Lys Ala Gln Asn Ser Glu Leu Ala Ser Thr Ala Asn Met Leu ^  ^
 a    a    a    a    a    TRANSLATION OF UNTITLED1 [A]  a    a    a    a    a 250                 260                 270                 280                 290                 300
CGT GAA CAG GTG GCA CAG CTT AAA CAG TTT GTC TTT AAA CAG GTC ATG AAC CAC GGT TGC GGC GGT TCT
GCA CTT GTC CAC CGT GTC GAA TTT GTC AAA CAG AAA TTT GTC CAG TAC TTG CCA CCA ACG CCG CCA AGA
Arg Glu Gln Val Ala Gln Leu Lys Gln Leu Lys Val Met Asn His Gly Cys Gly Ser ^  ^
 a    a    a    a    a    TRANSLATION OF UNTITLED1 [A]  a    a    a    a    a 310                 320
GGT GGC CAC CAT CAC CAT CAC CAT TAG           (SEQ ID NO: 40)
CCA CCG GTG GTA GTG GTA GTG GTA ATC
Gly Gly His His His His His His His *** ^   ^ (SEQ ID NO: 41)
 TRANSLATION OF UNTITLED1 [A]                 ^
```

FIG. 2

```
ATG GCT ACG CTC GTG TGT GAC ACC GTG CTG GAG GGG CAG TGG AGG GTC TGT
TAC CGA TGC GAG CAC ACA CTG TGG CAC GAC CTC ACC GTC CCC TCC CAG ACA
Met Ala Thr Leu Val Cys Asp Thr Val Leu Glu Gly Gln Trp Arg Val Cys >
       a    a    a_TRANSLATION OF F12JUN 6XHIS [A]   a    a    a   ^

AAC TGG GAG GGG CCC GGA GGA TCA GGT GGA GGA AGC GGA GGT GGT TCG
TTG ACC CTC CCC GGG CCT CCT AGT CCA GCT CCT TCG CCT CCA CCA AGC
Asn Trp Glu Gly Pro Gly Gly Ser Gly Gly Gly Ser Gly Gly Gly Ser >
      a    a    a_TRANSLATION OF F12JUN 6XHIS [A]  a    a    a  ^

GGA GGT GGA AGC GGA GGT GGT TCT AGA TGC GGT GGT CGG ATC GCC CGG CTA
CCT CCA CCT TCG CCT CCA CCA AGA TCT ACG CCA CCA GCC TAG CGG GCC GAT
Gly Gly Gly Ser Gly Gly Gly Ser Arg Cys Gly Gly Arg Ile Ala Arg Leu >
       a    a    a_TRANSLATION OF F12JUN 6XHIS [A]   a    a    a   ^

GAG GAA AAA GTG AAA ACC TTG AAA GCG CAA AAC TCC GAG CTG GCG TCC ACG
CTC CTT TTT CAC TTT TGG AAC TTT CGC GTT TTG AGG CTC GAC CGC AGG TGC
Glu Glu Lys Val Lys Thr Leu Lys Ala Gln Asn Ser Glu Leu Ala Ser Thr >
       a    a    a_TRANSLATION OF F12JUN 6XHIS [A]   a    a    a   ^

GCC AAC ATG CTC AGG GAA CAG GTG GCA CAG CTT AAA CAG AAA CAG GTC ATG AAC
CGG TTG TAC GAG TCC CTT GTC CAC CGT GTC GAA TTT GTC TTT CAG TAC TTG
Ala Asn Met Leu Arg Glu Gln Val Ala Gln Leu Lys Gln Leu Lys Val Met Asn >
       a    a    a_TRANSLATION OF F12JUN 6XHIS [A]   a    a    a  ^

GGT TGC GGC GGT TCT GGT GGC CAC CAT CAC CAT CAC CAC TGA  (SEQ ID NO:42)
CCA CCA ACG CCG CCA AGA CCA CCG GTG GTA GTG GTA GTG GTG ACT
Gly Gly Cys Gly Gly Ser Gly Gly His His His His His His *** >(SEQ ID NO:43)
       a    a    a_TRANSLATIONOF F112JUN 6XHIS [A]   a    a   ^
```

FIG. 5

SEQUENCE LISTING

```
<160> NUMBER OF SEQ ID NOS: 43

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Pro Asp Leu Leu Gly Gly Leu Phe Trp Val Trp Thr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic peptide

<400> SEQUENCE: 2

Lys Pro Asp Thr Ile His Ser Leu Phe His Val Val
1               5                   10
```

```
<210> SEQ ID NO 3
<211> LENGTH: 12
<212> TYPE: PRT
<213> ORGANISM: Artificial Sequence
<220> FEATURE:
<223> OTHER INFORMATION: synthetic peptide

<400> SEQUENCE: 3

Pro Val Gln Arg Leu His Asp Leu Phe Trp Leu Val
 1               5                  10

<210> SEQ ID NO 4
<211> LENGTH: 18
<212> TYPE: PRT
<213> ORGANISM: Artificial Sequence
<220> FEATURE:
<223> OTHER INFORMATION: synthetic peptide

<400> SEQUENCE: 4

Val Glu Pro Cys Thr Val Val Gly Cys Leu Phe Asn Val Val Gly Pro
 1               5                  10                  15

Ala Gly

<210> SEQ ID NO 5
<211> LENGTH: 18
<212> TYPE: PRT
<213> ORGANISM: Artificial Sequence
<220> FEATURE:
<223> OTHER INFORMATION: synthetic peptide

<400> SEQUENCE: 5

Pro Leu Glu Ile Cys Lys Leu Phe Asn Val Val Gly Leu Cys Asp Asn
 1               5                  10                  15

Gln Pro

<210> SEQ ID NO 6
<211> LENGTH: 18
<212> TYPE: PRT
<213> ORGANISM: Artificial Sequence
<220> FEATURE:
<223> OTHER INFORMATION: synthetic peptide

<400> SEQUENCE: 6

Gly Asp Val Ile Cys Asp Glu Leu Phe Cys Tyr Leu Gly Glu Glu Phe
 1               5                  10                  15

Ala Asn

<210> SEQ ID NO 7
<211> LENGTH: 17
<212> TYPE: PRT
<213> ORGANISM: Artificial Sequence
<220> FEATURE:
<223> OTHER INFORMATION: synthetic peptide

<400> SEQUENCE: 7

Trp Tyr Thr Glu Cys Glu Arg Val Leu Phe Asp Ser Tyr Cys Val Val
 1               5                  10                  15

Gly

<210> SEQ ID NO 8
<211> LENGTH: 18
<212> TYPE: PRT
<213> ORGANISM: Artificial Sequence
```

```
<220> FEATURE:
<223> OTHER INFORMATION: synthetic peptide

<400> SEQUENCE: 8

Ala Met Pro Phe Pro Cys Phe Glu Ala Met Phe Leu Cys Val Ala Asp
  1               5                  10                  15
Ser Val

<210> SEQ ID NO 9
<211> LENGTH: 18
<212> TYPE: PRT
<213> ORGANISM: Artificial Sequence
<220> FEATURE:
<223> OTHER INFORMATION: synthetic peptide

<400> SEQUENCE: 9

Lys Ala Pro Glu Cys Gly Val Cys Trp Gly Leu Phe Leu Cys Cys Ala
  1               5                  10                  15
Val Asp

<210> SEQ ID NO 10
<211> LENGTH: 18
<212> TYPE: PRT
<213> ORGANISM: synthetic peptide

<400> SEQUENCE: 10

Glu Val Trp Ser Cys Arg Pro Trp Gly Leu Phe Asn Leu Cys Tyr Glu
  1               5                  10                  15
Ala Ser

<210> SEQ ID NO 11
<211> LENGTH: 12
<212> TYPE: PRT
<213> ORGANISM: Artificial Sequence
<220> FEATURE:
<223> OTHER INFORMATION: synthetic peptide

<400> SEQUENCE: 11

Glu Glu Trp Leu Gly Ser Trp Thr Cys Ser Arg Thr
  1               5                  10

<210> SEQ ID NO 12
<211> LENGTH: 12
<212> TYPE: PRT
<213> ORGANISM: Artificial Sequence
<220> FEATURE:
<223> OTHER INFORMATION: synthetic peptide

<400> SEQUENCE: 12

Asp Leu Ser Leu Gly Tyr Tyr Ser Cys Thr Phe His
  1               5                  10

<210> SEQ ID NO 13
<211> LENGTH: 12
<212> TYPE: PRT
<213> ORGANISM: Artificial Sequence
<220> FEATURE:
<223> OTHER INFORMATION: synthetic peptide

<400> SEQUENCE: 13

Asp Leu Arg Ser Gly Phe Trp Val Cys Asn Leu Ala
  1               5                  10

<210> SEQ ID NO 14
```

```
<211> LENGTH: 18
<212> TYPE: PRT
<213> ORGANISM: Artificial Sequence
<220> FEATURE:
<223> OTHER INFORMATION: synthetic peptide

<400> SEQUENCE: 14

Pro Ser Trp Ile Cys Ser Ser Phe Ser Val Met Gly Phe Trp Val Cys
 1               5                  10                  15

Glu Asn

<210> SEQ ID NO 15
<211> LENGTH: 18
<212> TYPE: PRT
<213> ORGANISM: Artificial Sequence
<220> FEATURE:
<223> OTHER INFORMATION: synthetic peptide

<400> SEQUENCE: 15

Arg Gly Glu Thr Cys Glu Ala Met Arg Ile Leu Gly Pro Phe Trp Val
 1               5                  10                  15

Cys Met

<210> SEQ ID NO 16
<211> LENGTH: 18
<212> TYPE: PRT
<213> ORGANISM: Artificial Sequence
<220> FEATURE:
<223> OTHER INFORMATION: synthetic peptide

<400> SEQUENCE: 16

Glu Asp Tyr Glu Cys Ser Arg Ser Leu Thr Tyr Trp Val Cys Thr Val
 1               5                  10                  15

Pro Ser

<210> SEQ ID NO 17
<211> LENGTH: 12
<212> TYPE: PRT
<213> ORGANISM: Artificial Sequence
<220> FEATURE:
<223> OTHER INFORMATION: synthetic peptide

<400> SEQUENCE: 17

Glu Gln Ala Trp Val Cys His Arg Glu Asn Leu Trp
 1               5                  10

<210> SEQ ID NO 18
<211> LENGTH: 18
<212> TYPE: PRT
<213> ORGANISM: Artificial Sequence
<220> FEATURE:
<223> OTHER INFORMATION: synthetic peptide

<400> SEQUENCE: 18

Ser Glu Ile Glu Cys Val Lys Thr Ala Tyr Ala Trp Val Cys Gly Ala
 1               5                  10                  15

Arg Gly

<210> SEQ ID NO 19
<211> LENGTH: 18
<212> TYPE: PRT
<213> ORGANISM: Artificial Sequence
<220> FEATURE:
<223> OTHER INFORMATION: synthetic peptide
```

```
<400> SEQUENCE: 19

Glu Trp Val Cys Gly Glu Arg Ile Gly Glu Met Trp Ile Ser Cys Arg
 1               5                  10                  15
Gln Glu

<210> SEQ ID NO 20
<211> LENGTH: 17
<212> TYPE: PRT
<213> ORGANISM: Artificial Sequence
<220> FEATURE:
<223> OTHER INFORMATION: synthetic peptide

<400> SEQUENCE: 20

Val Trp Asp Cys Ala Arg Leu Gly Glu Ala Pro Phe Leu Lys Cys Leu
 1               5                  10                  15
Glu

<210> SEQ ID NO 21
<211> LENGTH: 18
<212> TYPE: PRT
<213> ORGANISM: Artificial Sequence
<220> FEATURE:
<223> OTHER INFORMATION: synthetic peptide

<400> SEQUENCE: 21

Thr Leu Val Cys Asp Thr Val Leu Glu Gly Gln Trp Arg Val Cys Asn
 1               5                  10                  15
Trp Glu

<210> SEQ ID NO 22
<211> LENGTH: 18
<212> TYPE: PRT
<213> ORGANISM: Artificial Sequence
<220> FEATURE:
<223> OTHER INFORMATION: synthetic peptide

<400> SEQUENCE: 22

Gly Glu Val Cys His Thr Leu Phe Gly Leu Trp Leu Ala Cys Glu Asn
 1               5                  10                  15
Pro Val

<210> SEQ ID NO 23
<211> LENGTH: 18
<212> TYPE: PRT
<213> ORGANISM: Artificial Sequence
<220> FEATURE:
<223> OTHER INFORMATION: synthetic peptide

<400> SEQUENCE: 23

Pro Gly His Gly Ser Thr Trp Ser Glu Met Ile Arg Glu Phe Glu Glu
 1               5                  10                  15
Met Val

<210> SEQ ID NO 24
<211> LENGTH: 12
<212> TYPE: PRT
<213> ORGANISM: Artificial Sequence
<220> FEATURE:
<223> OTHER INFORMATION: synthetic peptide

<400> SEQUENCE: 24

Tyr Ala Asp Trp Asp Ser Ile Cys Arg Leu Ala Phe
 1               5                  10
```

<210> SEQ ID NO 25
<211> LENGTH: 18
<212> TYPE: PRT
<213> ORGANISM: Artificial Sequence
<220> FEATURE:
<223> OTHER INFORMATION: synthetic peptide

<400> SEQUENCE: 25

Gly Thr Ile Cys Thr Trp Asp Ser Glu Thr Ser Ser Val Tyr Cys Gly
 1               5                  10                  15

Gly Ala

<210> SEQ ID NO 26
<211> LENGTH: 18
<212> TYPE: PRT
<213> ORGANISM: Artificial Sequence
<220> FEATURE:
<223> OTHER INFORMATION: synthetic peptide

<400> SEQUENCE: 26

Gly Asn Ile Cys Thr Phe Ala Arg Glu Thr Ser Thr Leu Asp Cys Ile
 1               5                  10                  15

Gly Pro

<210> SEQ ID NO 27
<211> LENGTH: 12
<212> TYPE: PRT
<213> ORGANISM: Artificial Sequence
<220> FEATURE:
<223> OTHER INFORMATION: synthetic peptide

<400> SEQUENCE: 27

Asp Asn Ala Trp Tyr Glu Arg Leu Glu Ser Cys Leu
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: synthetic peptide

<400> SEQUENCE: 28

Trp Tyr Glu Asn Ser Pro Phe Val Tyr Ile Glu Thr
 1               5                  10

<210> SEQ ID NO 29
<211> LENGTH: 18
<212> TYPE: PRT
<213> ORGANISM: Artificial Sequence
<220> FEATURE:
<223> OTHER INFORMATION: synthetic peptide

<400> SEQUENCE: 29

Tyr Asp Val Cys Val Phe Asp Ala Arg Tyr Ser Gln Leu Ser Cys Gln
 1               5                  10                  15

Ser Gln

<210> SEQ ID NO 30
<211> LENGTH: 18
<212> TYPE: PRT
<213> ORGANISM: Artificial Sequence
<220> FEATURE:
<223> OTHER INFORMATION: synthetic peptide

```
<400> SEQUENCE: 30

Ser Gly Pro Cys Arg Phe Asp Tyr Arg Thr Gly Glu Leu Leu Cys Ser
1               5                   10                  15

Leu Glu

<210> SEQ ID NO 31
<211> LENGTH: 18
<212> TYPE: PRT
<213> ORGANISM: Artificial Sequence
<220> FEATURE:
<223> OTHER INFORMATION: synthetic peptide

<400> SEQUENCE: 31

Asn Gly Cys Gly Thr Ile Phe Asn Cys Val Ser Glu Ala Arg Asp Val
1               5                   10                  15

Leu Pro

<210> SEQ ID NO 32
<211> LENGTH: 12
<212> TYPE: PRT
<213> ORGANISM: Artificial Sequence
<220> FEATURE:
<223> OTHER INFORMATION: synthetic peptide

<400> SEQUENCE: 32

Glu Cys Phe Asp Glu Arg Arg Gly Val Val Ala Cys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: synthetic peptide

<400> SEQUENCE: 33

Ser Leu Ala Gly Leu Glu Glu Leu Cys Leu Gly Met
1               5                   10

<210> SEQ ID NO 34
<211> LENGTH: 12
<212> TYPE: PRT
<213> ORGANISM: Artificial Sequence
<220> FEATURE:
<223> OTHER INFORMATION: synthetic peptide

<400> SEQUENCE: 34

Cys Gln Leu Ser Asp Gln Leu Gly Leu Ile Cys Ser
1               5                   10

<210> SEQ ID NO 35
<211> LENGTH: 18
<212> TYPE: PRT
<213> ORGANISM: Artificial Sequence
<220> FEATURE:
<223> OTHER INFORMATION: synthetic peptide

<400> SEQUENCE: 35

Glu Leu Ser Cys Asn Arg Asp Pro Ser Ile Pro Tyr Ile Leu Cys Ser
1               5                   10                  15

Ser Val

<210> SEQ ID NO 36
```

```
<211> LENGTH: 18
<212> TYPE: PRT
<213> ORGANISM: Artificial Sequence
<220> FEATURE:
<223> OTHER INFORMATION: synthetic peptide

<400> SEQUENCE: 36

Thr Gly Thr Cys Tyr Val Leu Ala Asp Trp Gly Val Leu Pro Cys Asp
 1               5                  10                  15

Asp Pro

<210> SEQ ID NO 37
<211> LENGTH: 20
<212> TYPE: PRT
<213> ORGANISM: Artificial Sequence
<220> FEATURE:
<223> OTHER INFORMATION: synthetic peptide

<400> SEQUENCE: 37

Ser Gly Asp Asp Tyr Cys Val Leu Val Phe Thr Asp Ser Ala Trp Thr
 1               5                  10                  15

Lys Ile Cys Asp
            20

<210> SEQ ID NO 38
<211> LENGTH: 28
<212> TYPE: PRT
<213> ORGANISM: Artificial Sequence
<220> FEATURE:
<223> OTHER INFORMATION: synthetic peptide

<400> SEQUENCE: 38

Ala Glu Ser Gly Asp Asp Tyr Cys Val Leu Val Phe Thr Asp Ser Ala
 1               5                  10                  15

Trp Thr Lys Ile Cys Asp Trp Ser His Phe Arg Asn
            20                  25

<210> SEQ ID NO 39
<211> LENGTH: 26
<212> TYPE: PRT
<213> ORGANISM: Artificial Sequence
<220> FEATURE:
<223> OTHER INFORMATION: synthetic peptide

<400> SEQUENCE: 39

Ser Gly Asp Asp Tyr Cys Val Leu Val Phe Thr Asp Ser Ala Trp Thr
 1               5                  10                  15

Lys Ile Cys Asp Trp Ser His Phe Arg Asn
            20                  25

<210> SEQ ID NO 40
<211> LENGTH: 330
<212> TYPE: DNA
<213> ORGANISM: Artificial Sequence
<220> FEATURE:
<223> OTHER INFORMATION: synthetic nucleic acid

<400> SEQUENCE: 40
atggctgaat cgggcgatga ctattgcgtt ctcgtttttca ccgactctgc gtggacaaag     60
atctgtgatt ggagccattt tcggaatggg cccggaggag gatcaggtgg aggaagcgga    120
ggtggttcgg gaggtggaag cggaggtggt tctagatgcg gtggtcgtat cgcccggctg    180
gaagaaaaag ttaagactct gaaagcgcaa aactctgaac tggcttccac cgcaaacatg    240
```

-continued

```
ctccgtgaac aggtggcaca gcttaaacag aaagtcatga accacggtgg ttgcggcggt      300
tctggtggcc accatcacca tcaccattag                                       330
```

<210> SEQ ID NO 41
<211> LENGTH: 109
<212> TYPE: PRT
<213> ORGANISM: SyArtificial Sequence
<220> FEATURE:
<223> OTHER INFORMATION: synthetic peptide

<400> SEQUENCE: 41

```
Met Ala Glu Ser Gly Asp Asp Tyr Cys Val Leu Val Phe Thr Asp Ser
 1               5                  10                  15

Ala Trp Thr Lys Ile Cys Asp Trp Ser His Phe Arg Asn Gly Pro Gly
                20                  25                  30

Gly Gly Ser Gly Gly Gly Ser Gly Gly Ser Gly Gly Gly Ser Gly
            35                  40                  45

Gly Gly Ser Arg Cys Gly Gly Arg Ile Ala Arg Leu Glu Glu Lys Val
        50                  55                  60

Lys Thr Leu Lys Ala Gln Asn Ser Glu Leu Ala Ser Thr Ala Asn Met
65                  70                  75                  80

Leu Arg Glu Gln Val Ala Gln Leu Lys Gln Lys Val Met Asn His Gly
                85                  90                  95

Gly Cys Gly Gly Ser Gly Gly His His His His His His
            100                 105
```

<210> SEQ ID NO 42
<211> LENGTH: 249
<212> TYPE: DNA
<213> ORGANISM: Artificial Sequence

<400> SEQUENCE: 42

```
aactgggagg ggcccggagg aggatcaggt ggaggaagcg gaggtggttc gggaggtgga       60
agcggaggtg gttctagatg cggtggtcgg atcgcccggc tagaggaaaa agtgaaaacc     120
ttgaaagcgc aaaactccga gctggcgtcc acggccaaca tgctcaggga acaggtggca     180
cagcttaaac agaaagtcat gaacggtggt tgcggcggtt ctggtggcca ccatcaccat     240
caccactga                                                             249
```

<210> SEQ ID NO 43
<211> LENGTH: 99
<212> TYPE: PRT
<213> ORGANISM: Artificial Sequence
<220> FEATURE:
<223> OTHER INFORMATION: synthetic peptide

<400> SEQUENCE: 43

```
Met Ala Thr Leu Val Cys Asp Thr Val Leu Glu Gly Gln Trp Arg Val
 1               5                  10                  15

Cys Asn Trp Glu Gly Pro Gly Gly Gly Ser Gly Gly Gly Ser Gly Gly
                20                  25                  30

Gly Ser Gly Gly Gly Ser Gly Gly Ser Arg Cys Gly Gly Arg Ile
            35                  40                  45

Ala Arg Leu Glu Glu Lys Val Lys Thr Leu Lys Ala Gln Asn Ser Glu
        50                  55                  60
```

```
Leu Ala Ser Thr Ala Asn Met Leu Arg Glu Gln Val Ala Gln Leu Lys
65                  70                  75                  80

Gln Lys Val Met Asn Gly Gly Cys Gly Gly Ser Gly Gly His His His
                85                  90                  95

His His His
```

SYNTHETIC PEPTIDES HAVING FGF RECEPTOR AFFINITY

CROSS-REFERENCE TO RELATED APPLICATIONS

This application claims benefit of priority to provisional patent applications Ser. No. 60/102,667, filed Sep. 30, 1998, and No. 60/134,120, filed May 14, 1999, the contents of which are incorporated herein by reference in their entirety.

FIELD OF THE INVENTION

The field of this invention is growth factors, particularly fibroblast growth factors.

BACKGROUND OF THE INVENTION

Basic fibroblast growth factors (bFGF)(also known as FGF2), so named because they contain a high number of basic amino acid residues (lysine, arginine and histidine) and therefore are cations at neutral pH, are potent mitogens for vascular endothelial cells in vitro and stimulate new capillary growth in vivo, i.e. they are angiogenic. Both human and bovine forms of basic FGF have been isolated, and the genes expressing these products have been cloned and sequenced. In addition, bFGF has been found to be expressed in a wide variety of tissue types, including pituitary, brain, adrenal gland, corpus luteum, retina, kidney, placenta, etc.

Patents of interest describing basic fibroblast growth factors include: U.S. Pat. Nos. 5,639,868; 5,604,293; 5,514,652; 5,478,740; 5,464,774; 5,459,015; 5,439,818; 5,352,589; 5,348,863; 5,331,095; 5,155,214; 5,143,829; 5,136,025; 5,130,418; 5,026,839; 4,994,559; 4,956,455.

Other References of interest include: Iwane et al, "*Expression of cDNA Encoding Human Basic Fibroblast Growth Factor in E. coli,*" Biochem. Biophys. Res. Comm. (1987) 146:470–477; Thompson et al, "*Cloning, Recombinant Expression, and Characterization of Basic Fibroblast Growth Factor,*" Methods Enzymol. (1991)198:96–116; Fox et al, "*Production, Biological Activity, and Structure of Recombinant Basic Fibroblast Growth Factor and an Analog . . . ,*" J. Biol. Chem. (1988) 263:18452–18458; Thompson et al, "*The Disulfide Structure of Bovine Pituitary Basic Fibroblast Growth Factor,*" J. Biol. Chem. (1992) 267:2269–2273; Conn et al, "*The Isolation and Purification of Two Anionic Endothelial Cell Growth Factors from Human Brain,*" Biochem. Biophys. Res. Comm.(1984) 124:262–268; Bohlen et al., "*Acidic Fibroblast Growth Factor (FGF) from Bovine Brain: Amino-Terminal Sequence and Comparison with Basic FGF,*" EMBO J. (1985) 4:1951–1956; Abraham et al., J. Cell. Biochem. (1987) Supplement, vol. 0, No. 11, p. 50, Abst No. 191; Guillermo Gimenez-Gallego et al., Biochem. Biophy. Res. Communications (1986)135: 541–548; Esch et al. Proc. Natl. Acad. Sci. USA, (1985) 82: 6507–6511; Bohlen et al., Proc. Natl. Acad. Sci., USA, (1984) 81: 5364–5368; Gospodarowicz et al., Biochem. Biophy. Res. Communications (1985) 128: 554–562.

SUMMARY OF THE INVENTION

Peptidic compositions capable of binding to the FGF receptor, as well as fusion proteins and oligomers of the same, are provided. The subject peptidic compositions are characterized by having substantially no sequence homology to known naturally occurring FGF receptor ligands and may further exhibit one or more FGF activities. The subject fusion proteins comprise the peptidic composition joined to an oligomerization (e.g. dimerization) domain, either directly or through a linker group and optionally further include a heparin binding domain. The subject compositions find use in a variety of applications, including diagnostic and therapeutic applications.

BRIEF DESCRIPTION OF THE FIGURES

FIG. 2 provides the nucleic acid and amino acid sequence of the C19jun fusion protein.

FIG. 5 provides the nucleic acid and amino acid sequence of the F12jun fusion peptide.

DEFINITIONS

Figure 1A:
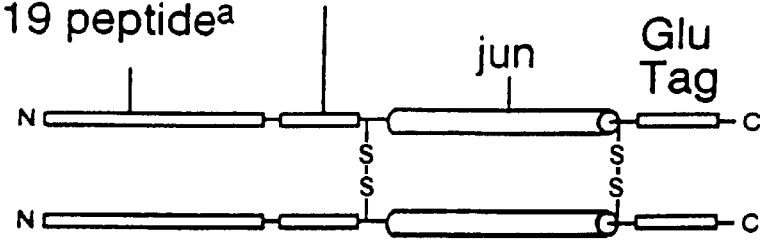
FIG. 1A provides a schematic representation of a homodimer according to the subject invention in which the two fusion proteins of the homodimer are joined by a jun dimerization domain.

The term "peptide" as used herein refers to any compound produced by amide formation between a carboxyl group of one amino acid and an amino group of another.

The term "polypeptide" as used herein refers to peptides with more than 10 to 20 residues.

The term "protein" as used herein refers to polypeptides of specific sequence of more than about 50 residues.

The term "expression system" (i.e. expression cassette) refers to DNA sequences containing a desired coding sequence and control sequences in operable linkage, so that hosts transformed with these sequences are capable of producing the encoded proteins. In order to effect transformation, the expression system may be included on a vector; however, the relevant DNA may also be integrated into the host chromosome.

DESCRIPTION OF THE SPECIFIC EMBODIMENTS

Peptidic compositions capable of binding to an FGF receptor, as well as fusion proteins and oligomers thereof, are provided. The subject peptidic compositions are characterized by having substantially no sequence identity with known naturally occurring FGF ligands and may exhibit one or more FGF activities. The subject fusion proteins comprise the peptidic compositions linked to an oligomerization domain, either directly or through a linking group and optionally further include a heparin binding domain. Also provided are methods of making the subject compositions. The subject compositions find use in a variety of applications, including diagnostic and therapeutic applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The peptidic compounds of the subject invention are characterized by being capable of specifically binding to at least one FGF receptor (FGFR). By capable of specifically binding with an FGF receptor is meant that the subject peptidic compounds bind to at least one FGF receptor with a $K_D$ value of at least about 1 μm, usually at least about 500 nM and more usually at least about 100 nM, where in many embodiments the subject peptidic compositions bind to FGF receptors with a $K_D$ value of at least about 10 nM. In addition to their ability to specifically bind to FGF receptors, the subject peptidic compounds may exhibit one or more activities exhibited by a naturally occurring FGF, particularly bFGF. bFGF activities that may be exhibited by the subject peptidic compounds include: (1) binding to, or displacement of, FGF from, immobilized FGF receptor extracellular domain and FGF receptor over expressing cells with high affinity ($IC_{50}$=8–37 nM); (2) specificity for the FGF versus the EPO receptor; (3) stimulation of FGF receptor autophosphorylation in Swiss 3T3 cells; (4) stimulation of MAP kinase phosphorylation in FGF receptor expressing cells, as exemplified by 293 cells; (5) stimulation of BrdU incorporation or cell proliferation in Swiss 3T3 or endothelial cells; (6) induction of neurite outgrowth in PC12 cells; (7) binding to heparin or a heparin related molecule, including, but not limited to, heparin, a heparin sulfate proteoglycan, and a heparin glycosoaminoglycan; and (7) stimulation of endothelial tube formation in vitro; where assays to detect the above activities are well known to those of skill in the art familiar with bFGF and its properties. Other bFGF activity assays in which the subject peptidic compounds may exhibit activity include: (1) in vitro and in situ growth factor binding assays, as described in Pontalino et al., Biochemistry (1994) 33: 10229–10248; Kiefer et al., Growth Factors (1991) 5:115–127; and U.S. Pat. No. 5,229,501; (2) cell proliferation assays, as described in U.S. Pat. No. 5,229,501; and the WST cell proliferation assay, Boehringer Mannheim); (3) in vivo and ex vivo assessments of angiogenesis, as described in Min et al., Cancer Res. (1996) 56: 2428–2433; and Bickness et al., Curr. Opin. Oncol. (1996) 8:60–65; (4) assessments of tumor growth, as described in Kim et al., Nature (1993) 362:841–844; and Millauer et al., Nature (1993) 367:576–579; (5) assessments of the ability to induce differentiation or lineage restriction, as, for example, described in Claude et al., Neuron (1988) 1:783–790; and (6) assessment of cell migration, as described in Piotrowicz et al., J. Cell. Physiol. (1999) 178:144–153.

The peptidic compounds range is size from 10 to 40 monomeric units, usually 10 to 35 monomeric units and more usually 10 to 30 monomeric units in length, where the term monomeric unit refers to an amino acid residue (e.g. one of the twenty naturally occurring α-amino acids); a non-naturally occurring amino acid residue; a substitute amino acid (e.g. N-substituted glycine), as that term is employed in WO 91/19735, the disclosure of which is herein incorporated by reference, and the like.

The subject peptidic compounds are characterized by having substantially no sequence identity with known naturally occurring bFGF ligands. Sequence similarity can be determined in a number of different manners. To determine sequence identity, sequences can be aligned using the methods and computer programs, including BLAST, available over the world wide web at http://ww.ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173–187 (1997). Also, the GAP program using the Needleman and Wunsch alignment method can be utilized to align sequences. See J. Mol. Biol. 48: 443–453 (1970).

Of interest is the BestFit program using the local homology algorithm of Smith Waterman (Advances in Applied Mathematics 2: 482–489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127–149, 1988, Alan R. Liss, Inc. Percent sequence identity is calculated by FastDB based upon the following parameters:

Mismatch Penalty: 1.00;

Gap Penalty: 1.00;

Gap Size Penalty: 0.33; and

Joining Penalty: 30.0.

One parameter for determining percent sequence identity is the "percentage of the alignment region length" where the strongest alignment is found.

The percentage of the alignment region length is calculated by counting the number of residues of the individual sequence found in the region of strongest alignment. This number is divided by the total residue length of the target or query polynucleotide sequence to find a percentage. An example is shown below:

```
Target sequence:    GCGCGAAATACTCACTCGAGG
                        |||  ||||  ||||
Query sequence:     TATAGCCCTAC.CACTAGAGTCC
                        1    5    10    15
```

The region of alignment begins at residue 9 and ends at residue 19. The total length of the target sequence is 20 residues. The percent of the alignment region length is 11 divided by 20 or 55%, for example.

Percent sequence identity is calculated by counting the number of residue matches between the target and query polynucleotide sequence and dividing total number of matches by the number of residues of the target or query sequence found in the region of strongest alignment. For the example above, the percent identity would be 10 matches divided by 11 residues, or approximately, 90.9%.

The percent of the alignment region length is typically at least about 55% of total length of the sequence, more typically at least about 58%, and even more typically at least about 60% of the total residue length of the sequence. Usually, percent length of the alignment region can be as great as about 62%, more usually as great as about 64% and even more usually as great as about 66%.

The subject peptidic compounds are unrelated to known naturally occurring FGF receptor ligands. As such, the peptidic compounds have substantially no sequence identity with the sequence of known naturally occurring FGF receptor ligands, specifically human or bovine naturally occurring bFGF as disclosed in U.S. Pat. No. 5,604,293, the disclosure of which is herein incorporated by reference. By substantially no sequence identity is meant that the sequence of residues in any one continuous stretch of 10 monomeric units of the peptidic composition has less than 60%, usually less than 50% and often less than 40% sequence identity with any stretch of amino acids of corresponding length found in naturally occurring FGF receptor ligands, particularly human or bovine bFGF, where sequence identity in many embodiments is as determined using the Smith-Waterman program with the BestFit program, as described above, in which the computer automatically selects the appropriate settings. For example, when any stretch of 15 monomeric units of the peptidic composition having at least 15 residues is matched or lined up with a stretch of corresponding length in either naturally occurring bovine bFGF or human bFGF, the number of residues that are the same or identical between the two sequences will not exceed about 9, and usually will not exceed 8 and more usually will not exceed 6. In many embodiments, the sequence identity between a given 10 to 30-mer or 10 to 30-residue long stretch of the peptidic composition and a stretch of either bovine or human bFGF of corresponding length will be less than 30%, often less than 25% and many times less than 20%. In other embodiments, the sequence identity may not exceed 15%, often 10% and more often 5%. Also included within the scope of the invention are those embodiments in which a stretch of residues in the peptidic composition has no sequence identity with a corresponding stretch in naturally occurring human or bovine bFGF.

The peptidic compounds may be polymers of: (a) naturally occurring amino acid residues; (b) polymers of non-naturally occurring amino acid residues, e.g. N-substituted glycines, amino acid substitutes, etc.; or (c) polymers of both naturally occurring and non-naturally occurring amino acid residues/substitutes. In other words, the subject peptidic compounds may be peptides or peptoids. Peptoid compounds and methods for their preparation are described in WO 91/19735, the disclosure of which is herein incorporated by reference.

Of particular interest in certain embodiments are peptides that include the following 5 residue long motif: L-F-X-V-V. A peptide is considered to have this particular motif if any 5 residue stretch of the peptide has at least one of: (a) three identical residues to the above motif in register; or (b) two identical residues and a third conservative substitution to the above motif in register or in minor registry shift. Specific peptides of this embodiment are characterized by having a 5 residue long sequence of the following formula:

$$\Psi\text{-F-X-}\Phi\text{-}\Omega$$

wherein $\Psi$ is L or another non-polar amino acid, specifically M, such that $\Psi$ is L or M;

X is any amino acid;

$\Phi$ is V or an uncharged amino acid, and may be serine or a non-polar amino acid, where specific non-polar amino acids of interest for this residue are L, Y, and C; and $\Omega$ is V or a non-polar amino acid, where specific non-polar amino acids of interest for this residue are: W, L, Y, and C.

Specific peptides of interest of this embodiment are:

A4 having the sequence: PDLLGGLFWVWT (SEQ ID NO:01)

A6 having the sequence: KPDTIHSLFHVV (SEQ ID NO:02)

E4 having the sequence: PVQRLHDLFWLV (ID NO:03)

C3 having the sequence: VEPCTVVGCLFNVVGPAG (SEQ ID NO:04)

E2 having the sequence: PLEICKLFNVVGLCDNQP (SEQ ID NO:05)

A2 having the sequence: GDVICDELFCYLGEEFAN (SEQ ID NO:06)

G11 having the sequence: WYTECERVLFDSYCVVG (SEQ ID NO:07)

D10 having the sequence: AMPFPCFEAMFLCVADSV (SEQ ID NO:08)

C10 having the sequence: KAPECGVCWGLFLCCAVD (SEQ ID NO:09)

E3 having the sequence: EVWSCRPWGLFNLCYEAS (SEQ ID NO:10)

Of particular interest in a second embodiment are peptides that include the following 5 residue long motif: G-F-W-V-C. A peptide is considered to have this particular motif if any 5 residue stretch of the peptide has at least one of: (a) three identical residues to the above motif in register; or (b) two identical residues and a third conservative substitution to the above motif in register or in minor registry shift. Specific peptides of this embodiment are characterized by having a 5 residue long sequence of the following formula:

$$\gamma\text{-}\delta\text{-}\zeta\text{-Z-C}$$

wherein $\gamma$, if present, is G or an amino acid selected from the group consisting of: P, T, Q, Y,E and L;

$\delta$ is F or an amino acid selected from the group consisting of: S, Y, A, E, V and W;

$\zeta$ is W or an amino acid selected from the group consisting of: Y, R and L; and Z is V or an amino acid selected from the group consisting of: T, S, D and A.

Specific peptides of interest in this embodiment are:

C6 having the sequence: EEWLGSWTCSRT (SEQ ID NO:11)

H6 having the sequence: DLSLGYYSCTFH (SEQ ID NO:12)

G5 having the sequence: DLRSGFWVCNLA (SEQ ID NO:13)

A1 having the sequence: PSWICSSFSVMGFWVCEN (SEQ ID NO:14)

C1 having the sequence: RGETCEAMRILGPEWVCM (SEQ ID NO:15)

G12 having the sequence: EDYECSRSLTYWVCTVPS (SEQ ID NO:16)

C4 having the sequence: EQAWVCHRENLW (SEQ ID NO:17)

B11 having the sequence: SEIECVKTAYAWVCGARG (SEQ ID NO:18)

E10 having the sequence: EWVCGERIGEMWISCRQE (SEQ ID NO:19)

E3 having the sequence: EVWSCRPWGLFNLCYEAS (SEQ ID NO:10)

A10 having the sequence: VWDCARLGEAPFLKCLE (SEQ ID NO:20)

F12 having the sequence: TLVCDTVLEGQWRVCNWE (SEQ ID NO:21)

F9 having the sequence: GEVCHTLFGLWLACENPV (SEQ ID NO:22)

Of particular interest in a third embodiment are peptides that include the following 4 residue long motif: T-W-D-S. A peptide is considered to have this particular motif if any 4 residue stretch of the peptide has at least one of: (a) three identical residues to the above motif in register; or (b) two identical residues and a third conservative substitution to the above motif in register or in minor registry shift. Specific peptides of this embodiment are characterized by having a 4 residue long sequence of the following formula:

$$\Theta\text{-}\lambda\text{-}\Sigma\text{-}\Xi$$

wherein

Θ is T or a charged amino acid, specifically D;

λ is W or a non-polar amino acid, specifically F;

Σ is D or an amino acid selected from the group consisting of A and S; and

Ξ is S or a charged amino acid, specifically R or E.

Specific peptides of interest of this third embodiment are:

B8 having the sequence: PGHGSTWSEMIREFEEMV (SEQ ID NO:23)

C5 having the sequence: YADWDSICRLAF (SEQ ID NO:24)

E11 having the sequence: GTICTWDSETSSVYCGGA (SEQ ID NO:25)

H12 having the sequence: GNICTFARETSTLDCIGP (SEQ ID NO:26).

Of particular interest in a fourth embodiment are peptides that include the following three residue long motif: W-Y-E. A peptide is considered to have this particular motif if any 3 residue stretch of the peptide has at least one of: (a) three identical residues to the above motif in register; or (b) two identical residues and a third conservative substitution to the above motif in register or in minor registry shift. Specific peptides of this embodiment are characterized by having a 3 residue long sequence of the following formula:

$$\text{W-Y-}\eta$$

wherein η is E or a polar amino acid, particularly T.

Specific peptides of interest falling within this embodiment are:

F6 having the sequence: DNAWYERLESCL (SEQ ID NO:27);

F5 having the sequence: WYENSPFVYIET (SEQ ID NO:28); and

G11 having the sequence: WYTECERVLFDSYCVVG (SEQ ID NO:07).

Of particular interest in a fifth embodiment are peptides that include the following 12 residue long motif: C-X-F-D-X-R-X-X-X-L-X-C. A peptide is considered to have this particular motif if any 12 residue stretch of the peptide has at least one of: (a) three identical residues to the above motif in register; or (b) two identical residues and a third conservative substitution to the above motif in register or in minor registry shift. Specific peptides of this embodiment are:

D11 having the sequence: YDVCVFDARYSQLSCQSQ (SEQ ID NO:29)

G10 having the sequence: SGPCRFDYRTGELLCSLE (SEQ ID NO:30)

The following peptides are also of interest:

A3 having the sequence: NGCGTIFNCVSEARDVLP (SEQ ID NO:31)

E5 having the sequence: ECFDERRGVVAC (SEQ ID NO:32)

D6 having the sequence: SLAGLEELCLGM (SEQ ID NO:33)

E6 having the sequence: CQLSDQLGLICS (SEQ ID NO:34)

E12 having the sequence: ELSCNRDPSIPYILCSSV (SEQ ID NO:35)

H10 having the sequence: TGTCYVLADWGVLPCDDP (SEQ ID NO:36)

Of particular interest in a sixth embodiment are peptides that include the following motif: $C(X_1)_n\pi(X_2)_mC$ where $X_1$ is D, E, or any amino acid; n=5–9; π is W or an amino acid selected from the group consisting of F and L; $X_2$ is any amino acid; and m is 1–3. Specific peptides of this embodiment are:

A1 having the sequence: PSWICSSFSVMGFWVCEN (SEQ ID NO:14)

C1 having the sequence: RGETCEAMRILGPFWVCM (SEQ ID NO:15)

G12 having the sequence: EDYECSRSLTYWVCTVPS (SEQ ID NO:16)

B11 having the sequence: SEIECVKTAYAWVCGARG (SEQ ID NO:18)

E10 having the sequence: EWVCGERIGEMWISCRQE (SEQ ID NO:19)

E3 having the sequence: EVWSCRPWGLFNLCYEAS (SEQ ID NO:10)

A10 having the sequence: VWDCARLGEAPFLKCLE (SEQ ID NO:20)

F12 having the sequence: TLVCDTVLEGQWRVCNWE (SEQ ID NO:21)

F9 having the sequence: GEVCHTLFGLWLACENPV (SEQ ID NO:22)

C19 having the sequence: AESGDDYCVLVFTDSAWTKICDWSHFRN, (SEQ ID NO:38)

Of particular interest in a seventh embodiment are peptides that include the following motif: $\xi(X_1)_nC$, where ξ is W or an amino acid selected from the group consisting of Y, F, and L; $X_1$ is any amino acid; and n=1–3. Specific peptides of this embodiment are:

C6 having the sequence: EEWLGSWTCSRT (SEQ ID NO:11)

H6 having the sequence: DLSLGYYSCTFH (SEQ ID NO:12)

G5 having the sequence: DLRSGFWVCNLA (SEQ ID NO:13)

A1 having the sequence: PSWICSSFSVMGFWVCEN (SEQ ID NO:14)

C1 having the sequence: RGETCEAMRILGPFWVCM (SEQ ID NO:15)

G12 having the sequence: EDYECSRSLTYWVCTVPS (SEQ ID NO:16)

C4 having the sequence: EQAWVCHRENLW (SEQ ID NO:17)

B11 having the sequence: SEIECVKTAYAWVCGARG (SEQ ID NO:18)

E10 having the sequence: EWVCGERIGEMWISCRQE (SEQ ID NO:19)

E3 having the sequence: EVWSCRPWGLFNLCYEAS (SEQ NO:10)

A10 having the sequence: VWDCARLGEAPFLKCLE (SEQ ID NO:20)

F12 having the sequence: TLVCDTVLEGQWRVCNWE (SEQ ID NO:21)

F9 having the sequence: GEVCHTLFGLWLACENPV (SEQ ID NO:22)

C19 having the sequence: AESGDDYCVLVFTDSAWTKICDWSHFRN, (SEQ ID NO:38)

Of particular interest in a further embodiment are peptides having a domain with a sequence of amino acid residues identical to or substantially the same as

SGDDYCVLVFTDSAWTKICD, (SEQ ID NO:37).

Of particular interest in this embodiment is a peptide having a sequence that is substantially the same as, or identical to:

AESGDDYCVLVFTDSAWTKICDWSHFRN (SEQ ID NO:38);

where the initial A and E residues may be optional and therefore may or may not be present, but in many embodiments will be present. The above sequence is also known as the "C19 clone" or the "C19 sequence". Thus, also of interest is the sequence

SGDDYCVLVFTDSAWTKICDWSHFRN (SED ID NO:39)

in which the leader A and E residues of C19 clone are absent.

In yet other embodiments of particular interest are peptides having the following sequence: TLVCDTVLEGQWRVCNWE (SEQ ID NO:21). This sequence is also known as the F12 clone or the F12 sequence.

Also of interest are peptides having a domain with a sequence of amino acid residues that is substantially the same as any of the sequences provided above, i.e., SEQ ID NOS: 1–39, where substantially the same as means that the compounds have sequence of residues that has at least about 40%, usually at least about 50% and more usually at least about 60% sequence identity with the above sequence, where sequence identity is measured as described above. For example, if a sequence is 22 amino acids in length, any given second sequence will be substantially the same as that sequence if the number of amino acids that are different between the two sequences does not exceed about 13, and preferably does not exceed about 11 and more preferably does not exceed about 9. In many embodiments, the percent sequence identity will be at least about 70%, usually at least about 75% and more usually at least about 80%. In many embodiments, the percent sequence identity will be at least about 85%, usually at least about 90%. In other embodiments, the percent sequence identity will be as high as 95%, usually as high as 97% and more usually as high as 99%.

Peptides or polypeptides comprising a sequence substantially the same as the sequences of the instant invention include mutants, fragments, and fusions exhibiting at least one bFGF activity. Typically, such variants exhibit at least 20%, usually at least 40%, and more usually at least 60% and in many embodiments at least 80% of at least one bFGF activity, where bFGF activities are reviewed supra.

Mutants of the instant sequences include residue, e.g. amino acid, additions, deletions, and substitutions. For example, mutants can be created by making conservative amino acid substitutions. The following are examples of conservative substitutions: Gly for Ala or vice versa; Val for Ile or Leu or vice versa; Asp for Glu or vice versa; Lys for Arg or vice versa; Asn for Gln or vice versa; and Phe for Trp or Tyr or vice versa, and the like. Mutants can be constructed using a nucleic acid coding sequence where any given codon is mutated to encode a corresponding conservative amino acid. For, example, in polynucleotides encoding the instant sequences, codons for the glycines can be substituted with codons for alanines. These coding sequences can be used to produce mutant peptides or polypeptides. Alternatively, such mutant peptides or polypeptides can be chemically synthesized. Once produced, these mutants can be assayed for bFGF activity by the methods described above.

A subset of mutants, called muteins, is a group of polypeptides with the non-disulfide bond participating cysteines substituted with neutral amino acids, generally, with serines. These mutants may be stable over a broader temperature range than cysteine containing peptides. In addition to disulfide bond participating cysteines, larger and/or charged residues, preferably, are retained and remain unchanged in mutant peptides or polypeptides. Such larger and/or charged residues can be a factor in forming peptide-protein interfaces. Other residues, such as prolines and glycines, are preferably retained and remain unchanged. Such amino acid residues can aid the peptide or polypeptide to adopt the proper backbone or three-dimensional structure.

Specifically, for mutants of the C19 clone, the cysteines at position 8 and 21, preferably, are retained to permit intra-peptide and inter-peptide disulfide bonds. In addition, one or more of the following amino acid residues is retained in the C19clone mutants: Glu2, Asp5, Asp6, Tyr7, Leu10, Phe12, Asp14, Trp17, Lys19, and Ile20. Mutants can comprise additions or deletions within the sequence. However, for the C19 clone, amino acids 9–20, preferably, are not deleted. More preferably, amino acids within residues 9–12 or 13–16 or 17–20 are not deleted.

Fragments differ from mutants or the instant sequences by amino and/or carboxyl terminal and/or internal amino acid deletions. The length of the deletion is not critical as long as the fragment retains its ability to bind to an FGF receptor. Typically the deletion is less than 25% of the total length of SEQ ID NOS:01–39; more typically the deletion is less than 20%, and even more typically the deletion is less than 15%, where percent is determined based on number of residues that are deleted. In many embodiments, the deletion is no more than 10% of the total length of SEQ ID NOS:01–39, usually no more than 5% and more usually no more than 1%. Generally, the deletion is less than 7, 6, 5, 4, 3, 2, or 1 amino acids. Preferably, for variants of the C19 clone, less than 7 amino acids are truncated from the—or C-terminus the C19 clone as shown in SEQ ID NO:38.

Fusion peptides are fragments, mutants, or the instant sequences with additional amino acids at either or both of the termini. The additional amino acid sequence is not necessarily homologous to any sequence found in SEQ ID NOS: 01–39.

Fusion proteins of the above peptidic compounds are also provided. In the fusion proteins of the subject invention, a peptidic compound as described above serves as a variable domain that is joined to an oligomerization domain, either directly or through a linking group. By oligomerization domain is meant a domain involved in association, usually covalent association, of two or more fusion proteins to produce higher order multimeric compounds, such as dimers, trimers, tetramers, pentamers etc. Of particular interest are dimerization domains which associate with each other to produce homodimers of the fusion proteins in which they are present, i.e. homodimerization domains.

The homodimerization domain contains a peptidic region capable of close association with an identical peptidic region under conditions found in the host, i.e. host conditions. The homodimerization domain will typically range in length from about 20 to 300 residues, and usually from about 25 to 100 residues. Specific peptidic regions of interest include at least portions of the following peptides, as well as fragments, homologues and derivatives thereof: transcription factors, such as GCNY (General Central Gene Y), MITF (microphthalmia transcription factor), EBNA1 (Epstein Barr virus nuclear antigen 1), TEF (transcriptional enhancer factor), DBP (D-site binding protein), Fc fragment of IgG, GCN4, Jun, particularly the leucine zipper of Jun, other naturally occurring leucine zippers, and the like, where a portion of Jun is preferred in many embodiments, specifically, the leucine zipper of Jun; and the Fc fragment of IgG is preferred in many other embodiments.

Higher order oligomerization domains are also encompassed within the scope of the invention. For example, the oligomerization domains may be a trimer or tetramer variant of GCN4, as describe in Harbury et al., Science (1993) 1401–1407.

In addition to the above listed naturally occurring oligomerization domains, mutants, fragments or fusions of the above listed naturally occurring oligomerization domains may also be employed.

Optionally, and to promote stable association of the oligomerization, e.g. homodimerization, domains, at either end of the central peptidic region of the homodimerization domain are cysteine residues, i.e. the central peptidic region is flanked at both the amino and carboxy termini with a cysteine residue. Therefore, in these embodiments, the homodimerization domain will generally be of the formula:

C-X-C wherein: C is cysteine, and X is any sequence encoding a peptide which is capable of closely associating with an identical peptide under host conditions. Thus, in a preferred embodiment, the homodimerization domain will be: C-leucine zipper of Jun-C.

Optionally, the variable and homodimerization domains may be separated by a linking domain of random or specific peptide sequence, or combination thereof, e.g. a randomer containing fixed cysteines or turn motifs such as an ala-pro sequence. When present, this linking domain may be anywhere from about 1 to 100 residues in length, but will usually not exceed 50 residues in length and more usually will not exceed 25 residues in length.

In many embodiments of the subject invention, in addition to the variable domain made up of the peptidic compound and the multimerization domain, the subject fusion proteins will also include a heparin binding domain. By heparin binding domain is meant a domain of residues which provides for binding to heparin, a heparin sulfate proteoglycan, a heparin glycosaminoglycan, or similar molecules. The characteristics of such domains are described in Hileman et al., Bioessays (February 1998)20:156–167. Assays for determining heparin binding activity include those described in Luster et al., J. Exp. Med. (1995) 182:219. In certain preferred embodiments, the heparin binding domain will be present as a feature of the multimerization domain. In other embodiments, the heparin binding domain may be the multimerization domain. Of particular interest in these embodiments is the use of jun as the multimerization domain, as it has been unexpectedly discovered by the Applicants that jun comprises a heparin binding domain. The heparin binding domain of jun can be readily determined by preparing fragments of the jun and testing such fragments in a heparin binding activity assay, such as those described in Luster et al., supra. In certain embodiments, the subject fusion protein may have just the peptidic domain and the heparin binding domain.

When a peptidic compound of the invention is to be used as an FGFR agonist, it preferably exhibits heparin binding. When a peptidic compound of the invention is to be used as an FGFR antagonist, it may lack heparin binding.

A preferred fusion protein according to the subject invention is a C19 fusion protein, where such a protein includes a peptide having a sequence which is substantially the same as or identical to the C19 sequence, described supra. Schematic representations of two specific C19 fusion proteins are provided in FIG. 1A and FIG. 1B, i.e. a C19jun fusion protein and dimer thereof and a C19IgG fusion protein and dimer thereof, respectively. Of particular interest in certain embodiments is a C19jun fusion protein, where a representative C19jun fusion protein is described in terms of its nucleotide and amino acid sequence in FIG. 2 and is identified as SEQ ID NOS:40 and 41, respectively, where the sequences show the 6-HIS tag, which may or may not be present. Fusion proteins having a sequence substantially the same as the C19jun sequence are those sharing at least about 40%, usually at least about 50% and more usually at least about 60% sequence identity. In many embodiments, the percent sequence identity will be at least about 70%, usually at least about 75% and more usually at least about 80%. In other embodiments, the percent sequence identity will be at least about 85%, usually at least about 90%. In yet other embodiments, the percent sequence identity will be as high as 95%, usually as high as 97% and more usually as high as 99%.

Another preferred fusion protein according to the subject invention is a F12 fusion protein, where such a protein includes a peptide having a sequence which is substantially the same as or identical to the F12 sequence, described supra. Of particular interest in certain embodiments is an F12jun fusion protein, where a representative F12jun fusion protein is described in terms of its nucleotide and amino acid sequence in FIG. 5 and is identified as SEQ ID NOS:42 and 43, respectively, where the sequences show the 6-HIS tag, which may or may not be present. Fusion proteins having a sequence substantially the same as the F12jun sequence of FIG. 5 are those sharing at least about 40%, usually at least about 50% and more usually at least about 60% sequence identity. In many embodiments, the percent sequence identity will be at least about 70%, usually at least about 75% and more usually at least about 80%. In other embodiments, the percent sequence identity will be at least about 85%, usually at least about 90%. In yet other embodiments, the percent sequence identity will be as high as 95%, usually as high as 97% and more usually as high as 99%.

Also provided by the subject invention are oligomers of the above peptidic compounds and fusion proteins. By oligomer is meant a compound having two or more of the above peptidic compounds or fusion proteins in close association, where the number of fusion proteins associated with each other in the oligomeric compound may be 3 or more, but will usually not exceed 6 and more usually will not exceed 5, where the oligomers are dimers in many preferred embodiments. The subject oligomers, in addition to or in lieu of any association provided by the oligomerization domain, if present, may be chemically cross-linked to provide for the covalent bonding of the individual components of the oligomeric compound. Chemical cross-linking means are well known to those of skill in the art and any convenient such means may be employed in the subject oligomers.

The subject peptidic compositions and fusion proteins thereof may be prepared using any convenient methodology. Thus, one may employ solid phase peptide synthesis techniques, where such techniques are known to those of skill in the art. See Jones, The Chemical Synthesis of Peptides (Clarendon Press, Oxford)(1994). Generally, in such methods a peptide is produced through the sequential additional of activated monomeric units to a solid phase bound growing peptide chain. Also of interest is the use of submonomers in solid phase synthesis, as described in WO 94/06451, the disclosure of which is herein incorporated by reference.

Instead of solid phase synthesis, the subject peptidic compositions, particularly the peptide compositions, and fusion proteins thereof, of the subject invention may be prepared through expression of an expression system comprising a polynucleotide encoding the peptidic composition or fusion protein. Any convenient methodology may be employed, where methodologies that may be employed typically include preparation of a nucleic acid encoding the subject peptide or fusion product, introduction of the encoding region into a vector for expression, transformation of a host cell with the vector, and expression and recovery of the product. Protocols for accomplishing each of the above steps are well known in art. See Sambrook, Fritsch & Maniatis, Molecular Cloning, A Laboratory Manual (Cold Spring Harbor Press, Inc.)(1989).

By "polynucleotide encoding the peptidic composition or fusion protein" is meant a nucleic acid composition comprising a sequence of DNA having an open reading frame that encodes the subject peptidic products and is capable, under appropriate conditions, of being expressed as the subject peptidic product. Also of interest are nucleic acids that are homologous or substantially similar or identical to these polynucleotides. By "homologous", "substantially similar", or "identical" is meant a nucleic acid sequence that has at least 75% sequence identity, usually at least 90%, more usually at least 95% with a polynucleotide sequence encoding the specific peptides listed above, as determined using a reference sequence of at least about 18 nt long, more usually at least about 30 nt long, and up to and including the complete sequence that is being compared, where sequence identity is determined using the BLAST algorithm, as described in Altschul et al. (1990), *J. Mol. Biol.* 215:403–10 (using the published default settings).

Sequence similarity can also be determined in other ways. In addition to the algorithms described above, sequence similarity between polynucleotides can be assessed empirically. For example, a polynucleotide sequence of the invention can hybridize to a test polynucleotide sequence under stringent conditions to form stable duplexes between homologous regions. Stable duplexes are those, for example, which would withstand digestion with a single-stranded specific nuclease(s), such as S1. Such duplexes can be analyzed by various methods, such as size determination of digested fragments.

"Hybridization" refers to the association of two nucleic acid sequences to one another by hydrogen bonding. Two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al., MOLECULAR CLONING: A LABORATORY MANUAL, SECOND EDITION (1989), Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook, et al., above at page 9.50.

Variables to consider when performing, for example, a Southern blot are (1) the complexity of the DNA being blotted and (2) the homology between the target and the sequences being detected. The total amount of the polynucleotides to be studied can vary a magnitude of 10, from 0.1 to 1 µg for a plasmid or phage digest to 109 to 108 µg for a single copy gene in a highly complex eukaryotic genome. For lower complexity polynucleotides, substantially shorter blotting, hybridization, and exposure times, a smaller amount of starting polynucleotides, and lower specific activity of a target polynucleotide can be used. For example, a single-copy yeast gene can be detected with an exposure time of only 1 hour starting with 1 µg of yeast DNA, blotting for two hours, and hybridizing for 4–8 hours with a target polynucleotide radiolabeled with 108 cpm/µg. For a single-copy mammalian gene a conservative approach would start with 10 µg of DNA, blot overnight, and hybridize overnight in the presence of 10% dextran sulfate using a target polynucleotide radiolabeled with greater than 108 cpm/µg, resulting in an exposure time of ~24 hours.

Several factors can affect the melting temperature ($T_m$) of a DNA-DNA hybrid between the target and sequence of interest, and consequently, the appropriate conditions for hybridization and washing. In many cases the target is not 100% homologous to the fragment. Other commonly encountered variables include the length and total G+C content of the hybridizing sequences and the ionic strength and formamide content of the hybridization buffer. The effects of all of these factors can be approximated by a single equation:

$$T_m = 81 + 16.6(\log 10\ Ci) + 0.4[\%\ G+C] - 0.6(\%\ \text{formamide}) - 600/n - 1.5(\%\ \text{mismatch}),$$

where Ci is the salt concentration (monovalent ions) and n is the length of the hybrid in base pairs (slightly modified from Meinkoth and Wahl, (1984) Anal. Biochem. 138: 267–284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the labeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a target polynucleotide with 95% to 100% sequence identity to the sequence to be detected, 37° C. for 90% to 95% sequence identity, and 32° C. for 85% to 90% sequence identity. For lower percentage sequence identity, formamide content should be lowered and temperature adjusted accordingly, using the equation above. If the homology between the target polynucleotide and the sequence to be detected are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel. Stringent conditions include hybridization in a solution of at least about 5×SSC at 65° C., or at least about 4×SSC at 42° C.; see, for example, U.S. Pat. No. 5,707,829, the disclosure of which is herein incorporated by reference.

Nucleic acids encoding the subject peptidic products can be prepared in a number of different ways. For example, the nucleic acid may be synthesized using solid phase synthesis techniques, as are known in the art. Oligonucleotide synthesis is also described in Edge et al., Nature (1981) 292:756; Duckworth et al., Nucleic Acids Res. (1981) 9:1691 and Beaucage & Caruthers, Tet. Letts (1981) 22:1859. Following preparation of the nucleic acid, the nucleic acid is then ligated to other members of the expression system to produce an expression cassette or system comprising a nucleic acid encoding the subject product in operational combination with transcriptional initiation and termination regions, which provide for expression of the nucleic acid into the subject peptidic product under suitable conditions.

Generally, a bacterial host will be transformed to contain the expression system using a vector. A variety of vectors may be employed so long as they introduce the expression system into the host in a manner whereby the product encoded by the expression system can be expressed. Thus, the vector could be one that is capable homologously recombining with a region of the host chromosome such that the expression system becomes integrated into the host chromosome such that expression of the protein encoded thereby can occur. See Thomas & Capecchi, Cell (1987) 51:503–512; as well as U.S. Pat. Nos.: 5,631,153; 5,627,059; 5,487,992 and 5,464,764, the disclosure of which is herein incorporated by reference.

Generally, the expression cassette will be a plasmid that provides for expression of the encoded peptidic product under appropriate conditions, i.e. in a host cell. The expression vector will typically comprise a replicon, which includes the origin of replication and its associated cis-acting control elements. Representative replicons that may be present on the expression vector include: pMB1, p15A, pSC101 and ColE1. Expression vectors generally have convenient restriction sites located near the promoter sequence to provide for the insertion of nucleic acid sequences encoding heterologous proteins. In addition, the expression vector will also typically comprise a marker which provides for detection of the clones that have been transformed with the vector. A variety of markers are known and may be present on the vector, where such markers include those that confer antibiotic resistance, e.g. resistance to ampicillin, tetracycline, chloramphenicol, kenamycin (neomycin), markers that provide for histochemical detection, etc. Specific vectors that may find use in the subject methods include: pBR322, pUC18, pUC19, πAN13, and the like. Introduction of the nucleic acid encoding the subject peptidic product into the expression vector is accomplished by cutting the expression vector and inserting the polynucleotide encoding the desired product.

Following preparation of the expression vector comprising the nucleic acid, the expression vector will be introduced into an appropriate host cell for production of the peptidic product, i.e. a host cell will be transformed with the expression vector. Transformation of host cells may be accomplished in any convenient-manner, where two representative means of transformation are treatment with divalent cation transformation compositions and electrotransformation. In transformation through divalent cation treatment, the host cells are typically incubated with the one or more divalent cations, e.g. $CaCl_2$, which serves to make the host cell permeable to the vector DNA. See Cohen et al., Proc. Nat'l. Acad. Sci. USA (1972) 69:2110. Other agents with which the host cells may also be incubated include DMSO, reducing agents, hexaminecobalt and the like, where such agents serve to improve the efficiency of transformation. In electrotransformation (also known as transformation by electroporation) host cells are subject to an electrical pulse in the presence of the vector in a manner sufficient for the vector to enter the host cells. See Dower et al., Nucleic Acids Research (1988) 16:6127.

A variety of host cells are suitable and may be used in the production of the peptidic product, were such host cells may be bacterial cells, yeast cells, or other cells, such as plant cells (see Depicker, J. Mol. Appl. Gen (1982) 1:561, where the host cell will generally be bacterial, e.g. E. coli, B. subtilis, S. cerevisiae, where an E. coli strain is often the host cell of choice. E. coli strains that may be used include DH1, DH5, MM294, LE392, MC1061 and JM109.

Following transformation, host cells are screened for incorporation of the expression vector. Transformed colonies, e.g. host cells harboring the expression vector with the nucleic acid encoding the peptidic product are identified, and then grown up in large quantity. Where appropriate, agents that induce expression of the peptidic product are contacted with the host cell, e.g. isopropylthiogalactoside (IPTG).

Following colony growth, the expressed product will be harvested and purified for subsequent use. Typically, purification of the product involves disruption of the host cell, inactivation and removal of the native host proteins and precipitation of the nucleic acids. The product is separated from the other host cell constituents using one or more of a number of separation techniques known to those of skill in the art, e.g. centrifugation, dialysis, gel filtration chromatography, ion exchange chromatography, and the like. See Guide to Protein Purification (Murray P. Deutscher ed., Harcourt Brace & Co.)(1990). Using these protein purification techniques, isolated product may be prepared, where by isolated is meant a composition that is at least about 95% by weight peptidic product, usually at least about 98% by weight peptidic product and more usually at least about 99% by weight product, when the composition is dehydrated, e.g. lyophilized.

The subject peptidic compounds, fusion proteins and oligomers thereof find use in variety of applications in which a specific ligand for an FGF receptor is desired, where such applications include both diagnostic and therapeutic applications. Representative applications are described below, but are in no way meant to be limiting on the total number of different types of applications in which the subject peptidic compounds, fusion proteins and oligomers thereof find use. The methods generally comprise administering to a host an effective amount of a peptidic compound of the invention, which may be part of a fusion protein as described above, or oligomerized, as described above, or coupled with a diagnostic or therapeutic agent. For some applications, the peptidic compound will be administered in a composition comprising an effective amount of the peptidic compound and a pharmaceutically acceptable excipient.

Diagnostic applications in which the subject compounds, fusion proteins and oligomers find use include applications in which the compounds are used as reagents, e.g. markers or labels, for identifying the presence of an FGF receptor on certain cell or tissue type, or fraction thereof. Thus, one can detect the presence of FGF receptors in a cellular or tissue sample by contacting the sample with a labeled peptidic compound of the subject invention. A variety of labels are known to those of skill in the art and include: radioisotopes, enzymes, fluorescers, chemiluminescers, or other labels for direct detection, which labels may be conjugated to the peptidic compound using methods known to those of skill in the art. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

In addition to diagnostic applications, the subject peptidic compositions, fusion proteins and oligomers thereof find use a variety of therapeutic applications. Therapeutic applications in which the subject compositions find use include applications in which one wishes to administer an FGF receptor antagonist and in applications where one wishes to administer an FGF receptor agonist.

FGF receptor antagonists have high affinity for an FGF receptor but lack at least one FGF activity. The subject peptidic compounds that find use as FGF receptor antagonists are those compounds which have high FGF receptor affinity but lack a multimerization domain and, optionally lack a heparin binding domain. Examples of such compounds include the C19 and F12 clones, described supra, as well as variants (i.e. homologues) thereof. Therapeutic applications in which ligands that act as FGF receptor antagonists find use include applications where one wishes to prevent the FGF receptor from binding to its natural ligand in vivo. Such situations include the modulation of conditions associated with neovascularization or angiogenesis, e.g. neoplastic diseases. Peptidic compounds with FGF receptor antagonist activity also find use as therapeutic agent targeting compounds, where the subject compound serves to direct the agent to a specific cell or target tissue that expresses an FGF receptor. Examples in which the subject peptidic compounds find use as targeting agents include: targeting DNA to specific cells expressing FGF receptors, as described in Sosnowski et al., J. Biol. Chem. (1996) 52: 33647–33653); targeting viral vectors to FGF receptor expressing cell types, as described in Rogers et al., Gene Therapy (1997) 4: 1387–1392; targeting of other therapeutic agents, e.g. small molecules, radionucleotides, chemotherapeutic agents, etc., where the therapeutic agent is conjugated to the subject peptidic compound; and the like. In some instances, it is desirable to conjugate an agent to the peptidic compound.

Alternatively, the subject peptidic compounds, fusion proteins or oligomers thereof may be used as FGF receptor agonists. In such situations, the subject compound is not only capable of high affinity binding to the FGF receptor, but is also capable of multimerization and, preferably, exhibits heparin binding activity. FGF agonists according to the subject invention find use in therapeutic agent targeting, as described above. Therapeutic applications in which FGF receptor agonists find use are those situations in which bFGF activity is desired, i.e. conditions in which one wishes to produce the cellular and tissue proliferative effects of bFGF. Such conditions include wound healing conditions, such as in musculo-skeletal conditions, e.g. bone fractures, ligament and tissue repair, tendonitis, bursitis, etc.; skin conditions, e.g. burns, cuts lacerations, bed sores; other wound healing situations, e.g. slow healing ulcers, etc.; conditions in which neovascularization or angiogenesis is desired, e.g. cardiac conditions; conditions in need of cell or tissue protection or regeneration, e.g. in the treatment of neurological conditions, e.g. neuro-degenerative diseases, such as stroke, Alzheimer's disease. Parkinson's disease, etc.; and the like.

Regardless of whether the compounds are employed as agonists or antagonists in therapeutic applications, by treatment is meant at least an amelioration of the symptoms associated with the disease or condition afflicting the host, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

In such methods, an effective amount of the subject peptidic compound, fusion protein or oligomer thereof, is administered to the host, where "effective amount" means a dosage sufficient to produce the desired amount of FGF receptor agonist or antagonist activity.

The peptidic compound, fusion protein or oligomer thereof, may be administered to the host using any convenient means capable of producing the desired result. Thus, the peptidic compound, fusion protein or oligomer thereof, can be incorporated into a variety of formulations for therapeutic administration. More particularly, the peptidic compound, fusion protein or oligomer thereof, of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the peptidic compound, fusion protein or oligomer thereof, can be achieved in various ways, including oral, buccal, rectal, parenteral, intraperitoneal, intradermal, transdermal, intracheal, etc., administration. In pharmaceutical dosage forms, the peptidic compound, fusion protein or oligomer thereof, may be administered alone or in combination with other pharmaceutically active compounds. The following methods and excipients are merely exemplary and are in no way limiting.

For oral preparations, the peptidic compound, fusion protein or oligomer thereof, can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The peptidic compound, fusion protein or oligomer thereof, can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The peptidic compound, fusion protein or oligomer thereof, can be utilized in aerosol formulation to be administered via inhalation. The compounds of the present invention can be formulated into pressurized acceptable propellants such as dichlorodifluoromethane, propane, nitrogen and the like.

Furthermore, the peptidic compound, fusion protein or oligomer thereof, can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

The therapeutic polynucleotides and polypeptides of the present invention can be introduced into a cell by a gene delivery vehicle. Generally, gene delivery vehicles can encode either polypeptides or polynucleotides, such as antisense or ribozymes. The gene delivery vehicle may be of viral or non-viral origin (see generally, Jolly. Cancer Gene Therapy (1994) 1:51–64; Kimura, Human Gene Therapy (1994) 5:845–852; Connelly, Human Gene Therapy (1995) 1:185–193; and Kaplitt, Nature Genetics (1994) 6:148–153). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/07936; WO 94/03622; WO 93/25698; WO 93/25234; U.S. Pat. No. 5,219,740; WO 93/11230; WO 93/10218; Vile and Hart, Cancer Res. (1993) 53:3860–3864; Vile and Hart, Cancer Res. (1993) 53:962–967; Ram et al., Cancer Res. (1993) 53:83–88; Takamiya et al., J. Neurosci. Res. (1992) 33:493–503; Baba et al., J. Neurosurg. (1993) 79:729–735; U.S. Pat. No. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67: ATCC VR-1247), Ross River virus (ATCC VR-373, ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovirus such as adeno-associated virus (AAV) vectors. Representative examples include the AAV vectors disclosed by Srivastava in WO 93/09239, Samulski et al., J. Vir. (1989) 63:3822–3828; Mendelson et al., Virol. (1988) 166:154–165; and Flotte et al., PNAS (1993) 90:10613–10617.

Representative examples of adenoviral vectors include those described by Berkner, Biotechniques (1988)

6:616–627; Rosenfeld et al., Science (1991) 252:431–434; WO 93/19191; Kolls et al., PNAS (1994) 91:215–219; Kass-Eisler et al., PNAS (1993) 90:11498–11502; Guzman et al., Circulation (1993) 88:2838–2848; Guzman et al., Cir. Res. (1993) 73:1202–1207; Zabner et al., Cell (1993) 75:207–216; Li et al., Hum. Gene Ther. (1993) 4:403–409; Cailaud et al., Eur. J. Neurosci. (1993) 5:1287–1291; Vincent et al., Nat. Genet. (1993) 5:130–134; Jaffe et al., Nat. Genet. (1992) 1:372–378; and Levrero et al., Gene (1991) 101:195–202. Exemplary adenoviral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, Hum. Gene Ther. (1992) 3:147–154 may be employed.

Other gene delivery vehicles and methods may be employed, including polycationic condensed DNA linked or unlinked to killed adenovirus alone, for example Curiel, Hum. Gene Ther. (1992) 3:147–154; ligand linked DNA, for example see Wu, J. Biol. Chem. (1989) 264:16985–16987; eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, Mol. Cell Biol. (1994) 14:2411–2418, and in Woffendin, Proc. Natl. Acad. Sci. (1994) 91:1581–1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 0 524 968.

Further non-viral delivery suitable for use includes mechanical delivery systems such as the approach described in Woffendin et al., Proc. Natl. Acad. Sci. USA (1994) 91(24):11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

Kits with unit doses of the subject compounds, usually in oral or injectable doses and often in a storage stable formulation, are provided. In such kits, in addition to the containers containing the unit doses will be an informational package insert describing the use and attendant benefits of the drugs in treating pathological condition of interest. Preferred compounds and unit doses are those described herein above.

The following examples are offered by way of illustration and not by way of limitation.

EXPERIMENTAL

Example 1

Preparation of p8 Phagemid Libraries

Random libraries of 12 and 18 mer peptides fused to the N-terminus of the M13 p8 coat protein were constructed using the method of Cwirla, et al (Proc Natl Acad Sci USA (1990) Aug; 87(16):6378–82). Libraries contained zero, one, or two fixed cysteine residues according to Table 1.

TABLE 1

Randomer p8 Phagemid Libraries Used to Identify Peptides Having FGF Receptor Affinity

| Library | # Independent Clones |
| --- | --- |
| 12mer (11 residue linker) A-$X_{12}$-(GGGS)$_2$GGG-p8 | 1.4 × 10$^9$ |
| 18mer (8 residue linker) A-$X_{18}$-(GGS)$_2$GG-p8 | 1.6 × 10$^9$ |
| 18mer with 2 cysteines mixture of: A-$X_3$-C-$X_{10}$-C-$X_3$-(GGS)$_2$GG-p8 A-$X_4$-C-$X_8$-C-$X_4$-(GGS)$_2$GG-p8 A-$X_5$-C-$X_6$-C-$X_5$-(GGS)$_2$GG-p8 | 2.0 × 10$^9$ |
| 18mer with 1 cysteine mixture of: A-$X_4$-C-$X_{13}$-(GGS)$_2$GG-p8 A-$X_8$-C-$X_9$- -(GGS)$_2$GG-p8 A-$X_{13}$-C-$X_4$-(GGS)$_2$GG-p8 | 2.0 × 10$^9$ |

Briefly, (+) strand oligonucleotides were designed to contain restriction site-compatible ends and sequence encoding random amino acids (NNS codons, where N is an equal mixture of all four bases and S is an equal mixture of G and C) and a flexible linker. These primers were annealed to (−) strand "adapter" oligonucleotides that complement the non-randomized ends of the randomer oligonucleotides and generate cohesive ends compatible with Hind III (5') and BamH1 (3') restriction sites, and the complex was ligated into the p8 display phagemid pMB 3.022. Ligation products were electroporated into *E. coli* and these cells were infected with M13K07 helper phagemid. Phagemids were harvested from cell supernatants after overnight growth by precipitation with 25% PEG 8000 containing 2.5M NaCl.

Example 2

Selection for FGFR-binding Phagemids

Wells of Nunc Immunosorp 96-well plates were coated overnight with 5.0 µg of goat anti-human IgG (Fc-specific) antibodies in 100 µL 50 mM Na$_2$CO$_3$, pH 9.6. Wells were blocked for 30 minutes with 200 µL PBS (0.01 M sodium phosphate, 0.1 M NaCl pH 7.5), 2% skim milk, rinsed with wash buffer (PBS +0.05% Tween 20), coated with 0.85 µg FGFR1c extracellular domain-IgG fusion protein in 100 mL binding buffer (RPMI, 25 mM HEPES, 1% BSA, 2% skim milk, 0.1% gelatin, and 0.05% Tween 20) for 1h, and washed again. Approximately 10$^{13}$ phagemids in 100 µL binding buffer were applied to both the FGFR-IgG-coated wells and control wells in which no FGFR-IgG had been added. Following a 2 hour incubation at room temperature, plates were was washed extensively (8×) and phage eluted by treatment with 100 µL of either 500 nM human thrombin in RPMI (rounds 1,3) or 0.2 M glycine, pH 2.2, 0.1% BSA and 0.05% Tween 20 (rounds 2,4) and shaking for 10 min. Acid eluates were neutralized with 7 µL 2 M Tris-Cl (pH 10). Eluates were used to infect 4 mL of log-phase *E. coli* cells (30 min at 37° C.). For thrombin eluates, cells were centrifuged briefly, supernatants discarded, and cells resuspended in 4 mL of 2YT media. Cells were then superinfected with 2.5×10$^{11}$ pfu VCS helper phage and grown in 25 mL 2YT broth containing 50 µg/mL carbenicillin for 18–24 h. Phage were harvested as described in Example 1 and the cycle repeated. Following 4 rounds of selection, titrations indicated ~10⁴-fold enrichment of phagemids eluated from FGFR-IgG containing wells versus those eluted from control (no FGFR-IgG) wells.

Example 3

Analysis of Individual Clones by Eu-labeled FGFR-IgG Binding to Immobilized Phagemid The immobilization of phagemid using antibodies, followed by probing with selected ligand in an ELISA format has been reported previously (Valadon, P. & Scharff, M. D., 1996 J. Immunol. Methods 197, 171–179). We developed a more sensitive detection method using Europium chelate-conjugated target receptor. The method was also extended to a displacement assay using unlabeled receptor, allowing determination of $IC_{50}$'s for the interaction of phage-displayed peptides and soluble target receptor.

Figure 7:
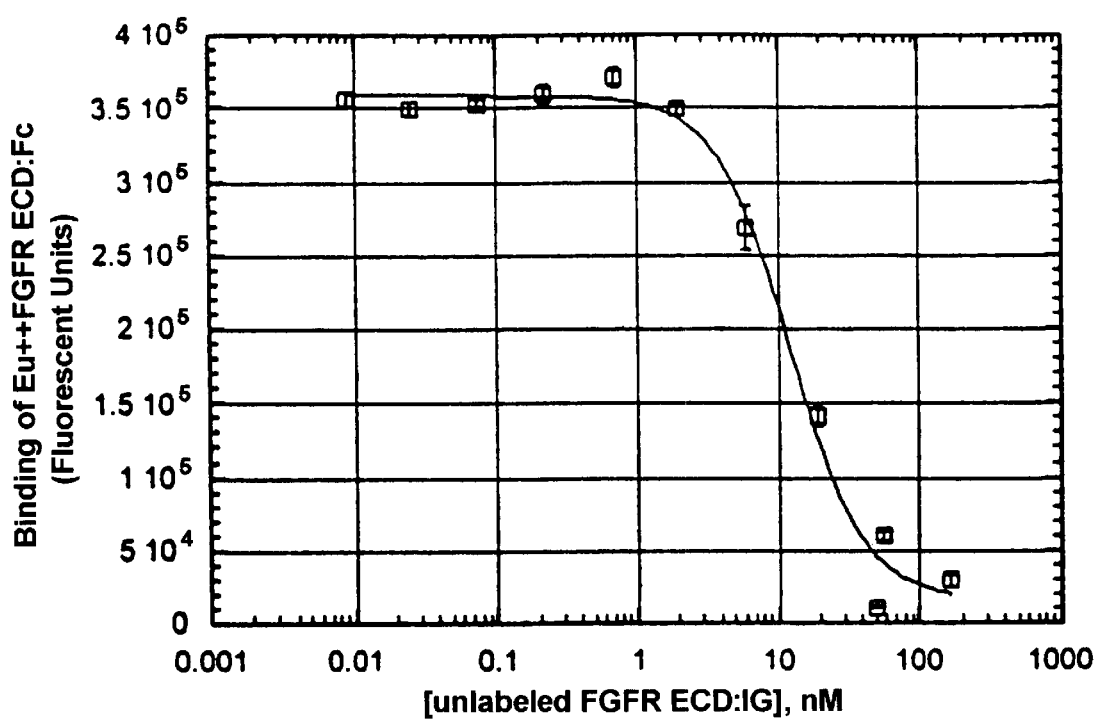
FIG. 7 provides a graph of the affinity of the F12 phagemid for FGFR.

Nunc Maxisorp 96-well plates were coated with 5 mg/ml anti-M13 antibody in 100 ml 50 mM $Na_2CO_3$ pH 9.6 and blocked using the conditions described in Example 2. Phagemid (~$10^{11}$ cfu) were applied to wells in binding buffer for 1 h and washed 6 times with PBS, 0.05% Tween 20, and 2 times with Delphia Wash Buffer (E&G Wallac). Serial dilutions of unlabeled FGFR-IgG were added along with a constant amount (500 pM–2.5 nM) of Europium-labeled FGFR-IgG in Delphia Assay Buffer (prepared according to instructions from E&G Wallac), and reactions allowed to incubate for 2 h. Wells were washed 8× in Delphia Wash Buffer, treated with 100 μL of Delphia Enhancer Solution and fluorescence measured. $IC_{50}$ values were determined from four-parameter fits to displacement plots. Results for the F12 clone are shown in FIG. 7, which shows an $IC_{50}$ of approximately 12 nM.

Example 4

Mitogenic Activity of F12-jun Fusion Protein

The sequence of the F12 clone insert was fused to (from $NH_2$— to COOH— terminus): 5 repeats of the sequence G-G-G-S as a flexible linker; the leucine zipper domain of c-jun (residues 276–314) flanked by cysteines to direct covalent homodimerization; a second short linker segment (G-G-S-G-G); and a polyhistidine affinity tag at the COOH-terminus in the pET23 vector. The nucleotide and amino acid sequences of F12jun6XHis are provided as SEQ ID NOS:42 and 43, respectively, shown in FIG. 5. This construct was expressed in BL21 DE3 pLysS *Escherichia coli* and purified by nickel-nitrilotriacetic acid metal-affinity chromatography as described by the kit manufacturer (Qiagen). Exponentially growing cultures were induced with 1 mM IPTG for 4 hrs at 37° C., lysed in 6M guanidine HCl, 5 mM imidazole, 0.1M $NaH_2PO_4$, 0.01M Tris-HCl, pH 8.0 and the protein purified under denaturing conditions. Purified protein was refolded by dilution with 5 volumes of 0.5 mM reduced glutathione, 0.5 mM oxidized glutathione, 1 mM EDTA, 0.01M Tris-HCl, pH 8.5, and 0.1M $NaH_2PO_4$, incubation for 24 hrs at 4° C., and subsequent extensive dialysis against phosphate buffered saline.

Figure 6:
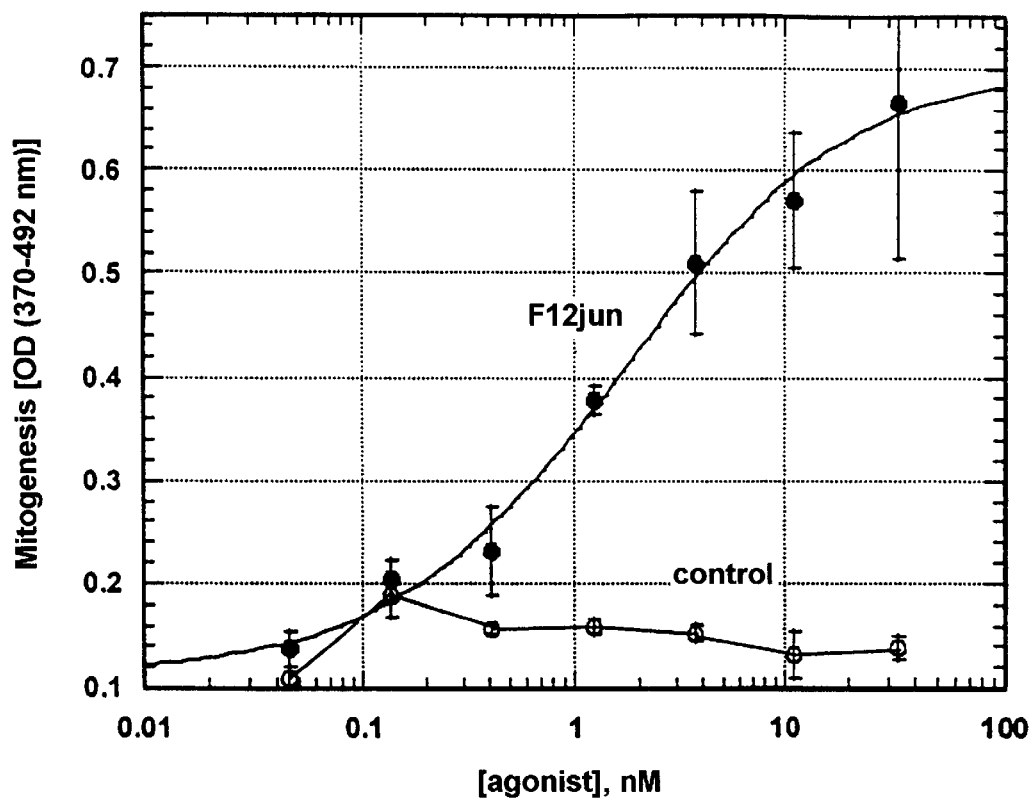
FIG. 6 provides a graph of the mitogenic activity of the F12jun fusion peptide.

Swiss 3T3 fibroblasts (1×10⁴ cells/well in 96-well microtiter plates) were incubated at 37° C. in quiescing media for 24 hrs, stimulated with an inactive control protein, or F12jun protein for 18 hrs in the presence of 15 U/ml heparin, labeled with BrdU for 4–6 hrs and assayed for BrdU incorporation by ELISA as described by the kit manufacturer (Boehringer Mannheim). Results indicated F12jun protein stimulated mitogenic activity in Swiss 3T3 fibroblasts at an $EC_{50}$ of approximately 1.7 nM. See FIG. 6.

Example 5

Expression and Purification of Clone 19-jun (C19-jun) protein.

Figure 1B:
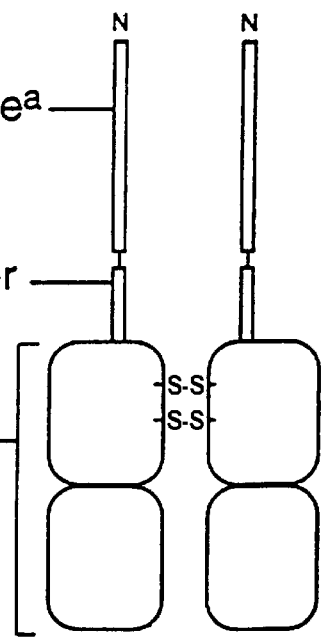
FIG. 1B provides a schematic of a homodimer according to the subject invention in which the two fusion proteins of the homodimer are joined by a hu IgG1-Fc domain.

A DNA construct encoding the fusion protein having a Clone 19 sequence, a flexible linker segment, the jun leucine zipper domain (as depicted in FIG. 1A) and a 6×Histidine tag at the COOH-terminus was cloned into a standard bacterial expression vector under the direction of the T7 promoter and transformed into standard *E. coli* strains.

To create an FGFR agonist, the C19 peptide insert sequence (SEQ ID NO:38) was fused in-frame with a protein domain that both mediated dimerization and bound heparin. The leucine zipper region of the transcription factor c-jun was chosen because it is small (39 amino acids), is well characterized structurally, forms homodimers when expressed in *Escherichia coli* (Riley et al. (1994) Eur. J. Biochem. 219:877–886), and binds heparin in vitro. The C19 sequence was fused to residues 276–314 of human c-jun through a flexible linker sequence, cysteines were placed on either end of the leucine zipper to direct covalent homodimerization (Crameri and Suter (1995) Gene 160:139; and deKruif and Logtenberg (1996) J. Biol. Chem. 271:7630–7634), and a polyhistidine tag was placed at the COOH-terminus for convenient affinity purification. The nucleotide sequence is provided in FIG. 2 as SEQ ID NO:40. This protein encoded thereby is designated C19-jun and its amino acid sequence is provided in FIG. 2 as SEQ ID NO:41. C19jun was cloned into the pET23 vector, and expressed in BL21 DE3 pLysS *Escherichia coli*.

C19-jun protein was expressed by treatment of exponentially growing cultures with IPTG for 4 hours at 37° C., and cells were lysed in buffer containing 6M guanidine HCl. Protein was purified under denaturing conditions with nickle NTA resin (Ni-NTA (nitriltriacetic acid) system including Ni-NTA agarose, Ni-NTA silica and Ni-NTA spin columns, from Quiagen, Chatsworth, Calif.), and re-folded at 4° C. for 24 hours in buffer containing 1M guanidine HCl, 0.1M Tris-HCl, pH 8.5, 0.1 M sodium phosphate, 1 mM EDTA, and 0.5 mM each oxidized and reduced glutathione. The protein was then dialyzed against PBS. The C19jun protein has the sequence shown in FIG. 2 (SEQ ID NO:41).

Purified C19-jun fusion protein (C19jun) was principally expressed as a 22 kDa homodimer, bound immobilized FGFR ECD protein in vitro with high affinity and specificity, as shown in Table 2, and quantitatively and specifically bound to heparin agarose beads through the leucine zipper domain. Table 2 gives approximate affinities of C19 variants for FGFR ECD. Apparent affinities for immobilized FGFR1c ECD were determined using BIAcore real-time kinetic analysis in the absence of heparin.

TABLE 2

| | $K_D$ (nM) |
|---|---|
| C19 synthetic peptide | 400 |
| jun leucine zipper only | >10,000 |
| C19jun | 10 |
| C19junΔhep | 10 |
| C19-Ig | 90 |

Example 6

Characterization of C19jun

A. Stimulation of FGFR Autophosphorylation and MAP Kinase Phosphorylation by Basic FGF (bFGF) and Clone 19-jun Protein (C19-jun)

To determine whether C19jun could activate FGF receptors in vivo, Swiss 3T3 cells were treated with basic FGF (bFGF) or purified C19jun protein. Cell extracts were then immunoprecipitated with anti-FGFR antibodies, analyzed by SDS-PAGE and immunoblotted with anti-phosphotyrosine antibodies. Extracts from bFGF and C19jun-stimulated 293 cells expressing FGFR1c were also immunoblotted with phospho-MAP Kinase-specific antibodies.

Swiss 3T3 fibroblasts, or 293 cells expressing full-length FGFRIc were incubated in quiescing media (DMEM, 1 µg/ml insulin, 5 µg/ml transferrin, 0.5 mg/ml BSA) for 24–48 hrs, and then stimulated with 1.0 nM bFGF or 50 nM refolded C19jun protein in the presence of 15 U/ml heparin for 15 minutes at 37° C. The cells were lysed and aliquots of lysate containing equal amounts of total protein were either analyzed directly by immunoblotting with phospho-MAPKspecific antibodies and anti-total MAPK antisera (New England Biolabs) or immunoprecipitated with anti-FGFR antisera and immunoblotted with anti-phosphotyrosine antibodies (Upstate Biotechnology, Inc.). Both bFGF and C19jun induced FGFR autophosphorylation and MAP kinase phosphorylation. These results demonstrate that C19jun can activate FGF receptors in cells and initiate intracellular signaling.

B. Stimulation of Mitogenesis of Swiss 3T3 Fibroblasts by Basic FGF (bFGF) and Clone 19-jun Protein (C19-jun)

Figure 3:
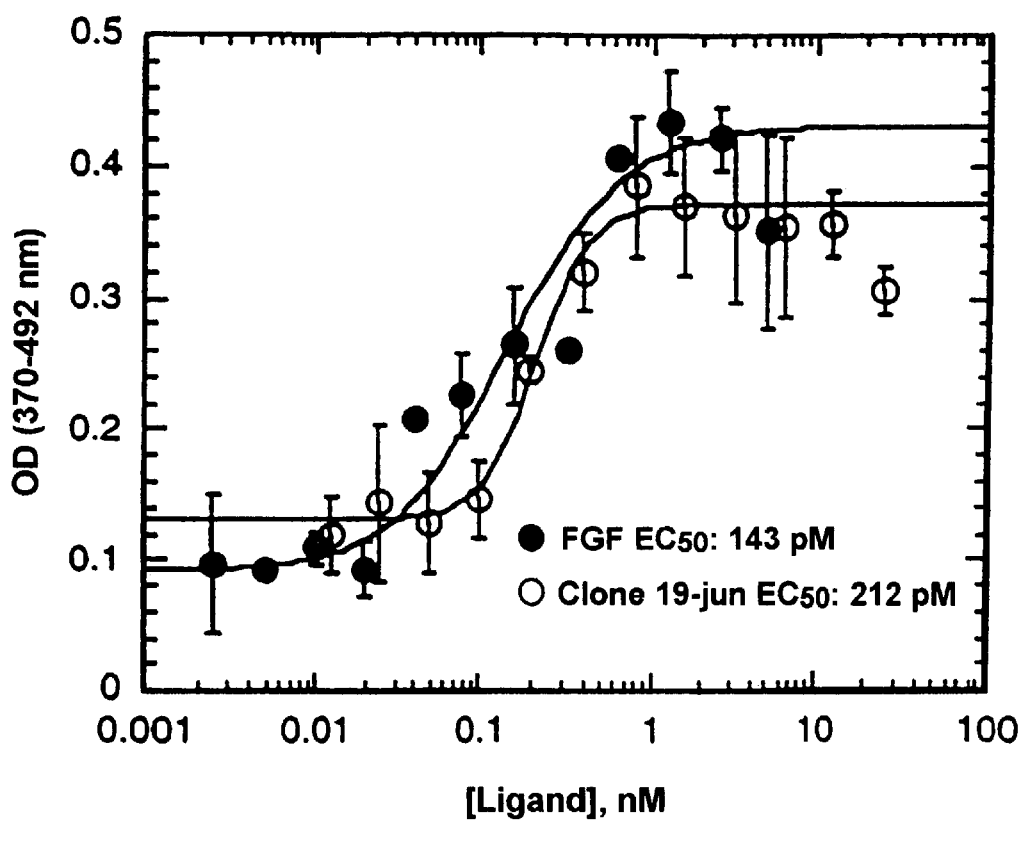
FIG. 3 is a graph showing the activity of the C19jun fusion protein in a BrdU incorporation assay.

6×Histidine-tagged Clone 19-jun protein (FIG. 1A) was expressed in bacteria and purified by metal affinity chromatography as described in Example 5. Assay of BrdU incorporation, a measure of entry of cells into S-phase and therefore of mitogenesis, was performed according to manufacturers instructions (Cell proliferation ELISA, BrdU, Cat. No. 1-647-229, Boehringer-Mannheim, Indianapolis, Ind.). Briefly, $1 \times 10^4$ Swiss 3T3 cells per well were plated on gelatin-coated 96-well microtiter plates in complete media (DMEM, 10% FCS, antibiotics), incubated 24 hours, and the media changed to quiescent media for an addition 24 hours (DMEM containing 0.5 mg/ml bovine serum albumin, 1 µg/ml insulin, 5 µg/ml transferrin, antibiotics). The cells were then treated with bFGF or Clone 19-jun protein at the indicated concentrations in the presence of 15 U/ml heparin. 18 hours later, BrdU was added, the cells incubated an additional 4 hours, and assayed as described. The results show that C19-jun protein stimulates mitogenesis in Swiss 3T3 cells with a potency similar to that of bFGF (EC50 240 pM vs. 140 pM). See FIG. 3. Heparin alone had no effect, nor did a control protein expressed and purified in the same manner in which the C19 sequence was deleted. C19jun (2 nM) also stimulated proliferation of these cells in long term assays to an equal or greater extent than 1 nM bFGF. C19jun also stimulated the proliferation of human endothelial cells in similar assays, demonstrating that C19jun reproduces the mitogenic effects of bFGF on multiple FGF-responsive cell types.

Example 7

Stimulation of Swiss 3T3 Proliferation by bFGF and C19-jun

Figure 4:
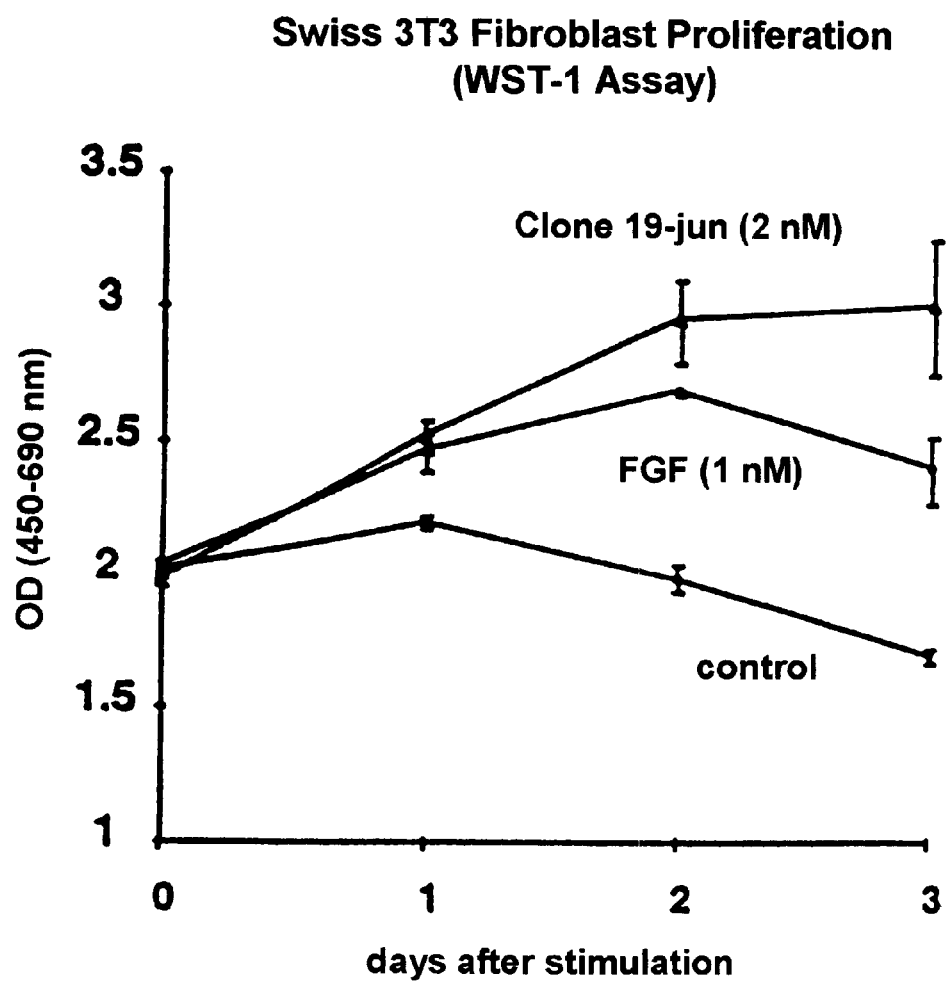
FIG. 4 is a graph showing the activity of the C19jun fusion protein in the WST-1 assay.

Swiss 3T3 cells were plated on gelatin-coated 96-well microtiter plates in quiescent media containing the indicated concentrations of bFGF or C19-jun protein and 15 U/ml heparin and cell number estimated on each of 4 successive days by the WST-1 assay as per manufacturers instructions (Cell proliferation Reagent WST-1, no. 1644807, Boehringer-Mannheim). The results show that C19-jun stimulates Swiss 3T3 fibroblast proliferation as well or better than bFGF. See FIG. 4.

Example 8

Induction of PC12 Cell Neurite Outgrowth $1 \times 10^4$ PC12 cells per well were plated on mouse laminin-and-poly-L-lysine-coated 24-well plates in 1 ml of media (RPMI 1640, 10% horse serum, 5% FCS, antibiotics) and stimulated with 1 nM bFGF or 2 nM C19-jun protein in the presence of 15 U/ml heparin for 4 days. The appearance of neurite extensions in bFGF- and C19-jun-treated cells, but not in control (heparin-treated only) cells indicated that C19-jun induces PC12 cell differentiation as well or better than bFGF.

Example 9

C19jun is a Specific FGFR Agonist

To further examine the specificity of C19jun for FGFR, Swiss 3T3 cells were stimulated with C19jun in the presence of protein representing the soluble extracellular binding domain (ECD) of various receptors used as binding competitors. The mitogenic activity of C19jun was abolished by pre-incubation of the fusion protein with excess FGFR1c ECD, but was unaffected by incubation with identical concentrations of the closely related PDGF receptor ECD or with erythropoietin receptor ECD. As an additional test, the activities of C19jun and bFGF were assayed in L6 myoblast cell lines stably expressing FGFR1c and in control L6 cells that do not express FGFR (Werner et al. (1992) Mol. Cell. Biol. 12:82–88). Both bFGF and C19jun stimulated c-fos mRNA expression in the FGFR-expressing cells, but neither was active in control cells. Similar results were observed when phosphorylation of MAPK was analyzed in these cells. These results demonstrate that C19jun activity is specific for the FGFR, and requires the presence of the FGFR for activity.

Example 10

Structure-function Analysis of C19jun

The structural requirements for C19jun activity were investigated by analysis of the activity of deletion mutants a point mutation analysis. Truncation of the C-terminal 7 amino acids of C19 (SEQ ID NO:38) was found to result in an approximately 15-fold loss of affinity for FGFR. Internal deletion of amino acids 2–6; 9–12; 13–16; or 17–20 resulted in loss of measurable FGFR binding.

Protein representing the linker segments and c-jun leucine zipper without the C19 sequence (FIG. 2) was expressed, purified, and characterized as for C19jun. C19 peptide with an intrapeptide disulfide bond was synthesized, purified by HPLC, and characterized by mass spectroscopy. C19junΔhep protein was prepared by changing human c-jun residues Arg276, Arg279, Lys285, and Lys288 in the leucine zipper domain to glutamines. Expression, purification, and characterization was as for C19jun. C19-Ig fusion protein was prepared by cloning the C19 sequence and GGGS linker segments (FIG. 1B) in frame with the Fc portion of human IgG1, expressing the protein in baculovirus and purifying protein with protein A affinity chromatography. The approximate apparent affinities ($K_D$) of C19 synthetic peptide, jun leucine zipper, C19jun, C19junΔhep and C19-Ig fusion proteins for immobilized FGFR ECD protein in the absence of heparin were determined by real-time kinetic analysis using the BIAcore biosensor (Pharmacia) and published methods(Laminet et al. (1996) J. Biol. Chem. 271:265) and are shown in Table 2, supra. The extracellular ligand-binding domain of human FGFR Ic (residues 1–377) and human erythropoietin receptor (residues 1–250) were fused to the Fc region of human IgG1, expressed in baculovirus and purified by protein A affinity chromatography. Activity of the fusion proteins was confirmed by binding of [$^{125}$I]-labeled ligands. PDGF receptor Fc fusion protein was from R&D Systems.

Deletion of the C19 sequence from the fusion protein abrogated mitogenic activity. Further, a synthetic peptide containing only the C19 sequence, but not the c-jun leucine zipper domain, did not induce mitogenesis even at high concentrations. These experiments demonstrate that both the C19 peptide and the leucine zipper domain are required for agonist activity.

C. Contribution of Heparin Binding to C19jun Activity

To determine the importance of heparin to C19jun activity, Swiss 3T3 fibroblasts were stimulated with C19jun in the presence and absence of heparin. The addition of heparin was required for optimal mitogenic activity of the C19jun fusionprotein. Heparin was also required for the morphogenic activity of C19jun on PC12 cells. To determine whether the heparin-binding site on C19jun was required for activity, 2 lysines and 2 arginines predicted to comprise a major portion of the heparin-binding site in the c-jun leucine zipper domain were changed to glutamines. The mutated C19jun protein (C19junΔhep) was expressed as a homodimer and bound FGFR ECD in the absence of heparin with the same apparent affinity as C19jun. However, unlike C19jun, C19junΔhep protein had very low affinity for heparin and was inactive in Swiss 3T3 mitogenesis assays. Similar results were obtained when the c-jun leucine zipper was replaced with the Fc portion of IgG1 (C19-Ig), which also mediates spontaneous dimerization but does not bind heparin. C19-Ig was also expressed as a homodimer and bound FGFR with high apparent affinity ($K_D$=90 nM), but bound heparin poorly and did not stimulate mitogenesis at concentrations up to 1 μM. Pre-incubation of cultures with 1 μM C19-Ig completely inhibited C19jun-induced mitogenic activity, demonstrating that C19-Ig was competent for receptor binding, but not for receptor activation. Taken together, these experiments demonstrate that the interaction of heparin with C19jun is essential for stimulation of mitogenesis.

It is evident from the above results and discussion that novel peptides having high affinity for the FGF receptor have been identified. The subject peptides, depending on their specific nature, find use as either FGF receptor antagonists or agonists, and therefore find use in a variety of different research and therapeutic applications. Importantly, the subject peptides provide alternatives to naturally occurring or synthetic bFGF. As the subject peptides are smaller than bFGF, they provide for easier administration and use. Furthermore, they are easier and less expensive to manufacture. As such, the subject invention provides for a significant advance in the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A peptidic compound that binds to a fibroblast growth factor (FGF) receptor, wherein said peptidic compound comprises the sequence Ψ-F-X-Φ-Ω, wherein Ψ is L or M, X is any amino acid, Φ is V, L, Y, or C, and Ω is V, W, L, Y, or C, and wherein said peptidic compound has a length of from 10 to 40 monomeric units.

2. The peptidic compound according to claim 1, wherein said peptidic compound is an FGF receptor agonist.

3. The peptidic compound according to claim 2, wherein said peptidic compound exhibits at least one bFGF activity selected from the group consisting of: (a) displacement of bFGF from an FGF receptor; (2) stimulation of MAP kinase phosphorylation in FGF receptor expressing 293 cells; (3) stimulation of FGF receptor autophosphorylation; and (4) stimulation of BrdU incorporation in Swiss 3T3 cells.

4. The peptidic compound according to claim 1, wherein said peptidic compound is a peptide.

5. The peptidic compound according to claim 1, wherein said peptidic compound comprises a sequence selected from the group consisting of SEQ ID NOS:1–10 [SEQ ID NOS:1–39].

6. An oligomer of a peptidic compound according to claim 1.

7. The oligomer according to claim 6, wherein said oligomer is a homodimer.

8. The homodimer according to claim 7, wherein said homodimer is a dimer of a fusion protein according to claim 1.

9. The peptidic compound of claim 1, wherein said FGF receptor (FGFR) is FGFR1c.

10. A fusion protein comprising:

(a) the amino acid sequence of the peptidic compound of claim 1, and (b) an oligomerization domain.

11. The fusion protein of claim 10, wherein said fusion protein further comprises a heparin binding domain.

12. The fusion protein of claim 10, wherein said fusion protein is an FGF receptor agonist.

* * * * *